United States Patent
Heimbrock et al.

(10) Patent No.: US 6,249,923 B1
(45) Date of Patent: Jun. 26, 2001

(54) ADJUSTABLE HEAD REST FOR A PATIENT SUPPORT

(75) Inventors: Richard H. Heimbrock, Cincinnati; Patrick J. Minnelli, Harrison, both of OH (US); James L. Walke, Batesville, IN (US)

(73) Assignee: Hill-Rom, Inc., Batesville, IN (US)

( * ) Notice: Subject to any disclaimer, the term of this patent is extended or adjusted under 35 U.S.C. 154(b) by 0 days.

(21) Appl. No.: 09/369,546

(22) Filed: Aug. 6, 1999

Related U.S. Application Data

(62) Division of application No. 08/892,147, filed on Jul. 14, 1997, now Pat. No. 6,076,208.

(51) Int. Cl.[7] .................................................. A61G 7/07
(52) U.S. Cl. .......................... 5/622; 5/639; 5/640; 5/643
(58) Field of Search ............................. 5/622, 636, 637, 5/639, 640, 643; 297/408

(56) References Cited

U.S. PATENT DOCUMENTS

| | | |
|---|---|---|
| 477,449 | 6/1892 | Pirrung . |
| 1,626,091 | 4/1927 | Macklin . |
| 2,042,399 | 5/1936 | Holme . |
| 2,258,782 | 10/1941 | McKean . |
| 2,972,505 | 2/1961 | Weickgenannt . |
| 3,041,121 | 6/1962 | Comper . |
| 3,227,440 | 1/1966 | Scott . |
| 3,304,116 | 2/1967 | Stryker . |
| 3,411,766 | 11/1968 | Lanigan . |
| 3,572,835 * | 3/1971 | Kees, Jr. et al. ............. 5/640 X |
| 3,733,620 | 5/1973 | Glintz . |
| 3,858,937 * | 1/1975 | Norris ......................... 297/408 |
| 3,885,831 * | 5/1975 | Rasmussen ................... 297/410 |
| 3,929,309 | 12/1975 | De Vore . |

(List continued on next page.)

FOREIGN PATENT DOCUMENTS

| | | |
|---|---|---|
| 3538887 A1 | 5/1986 | (DE) . |
| 2 547 195 | 12/1984 | (FR) . |
| 2 585 240 | 1/1987 | (FR) . |
| 40-23833 | 10/1965 | (JP) . |
| 42-1715 | 1/1967 | (JP) . |
| 42-11267 | 6/1967 | (JP) . |
| 52-7276 | 1/1977 | (JP) . |
| 53-74190 | 7/1978 | (JP) . |
| 53-74191 | 7/1978 | (JP) . |
| 58-127648 | 7/1983 | (JP) . |
| 58-143753 | 8/1983 | (JP) . |
| 61-226043 | 10/1986 | (JP) . |

OTHER PUBLICATIONS

Reliance M–701 Surgical Stretcher, "Mobile Surgical Stretcher", 2 pages, date unknown.

Stryker Patient Handling, "Head/Neck Surgery Stretcher Model 1067", 2 pages, Dec. 1992.

Hausted, "Products for Head and Neck Surgery", 4 pages, date unknown.

(List continued on next page.)

*Primary Examiner*—Michael F. Trettel
(74) *Attorney, Agent, or Firm*—Barnes & Thornburg

(57) ABSTRACT

An apparatus is provided for supporting a patient. The apparatus includes a frame, a patient-support deck coupled to the frame and configured to support the patient, and a bracket coupled to the patient-support deck for pivoting movement about a transverse first pivot axis. The bracket extends away from the patient-support deck. The apparatus also includes a head rest having first and second spaced-apart sides which is coupled to the bracket for pivoting movement about a transverse second pivot axis, and a grip handle coupled to the head rest. The grip handle has a side handle portion extending alongside the first side of the head rest in spaced-apart relation therewith so that the side handle portion can be grasped to control pivoting movement of the head rest relative to the patient-support deck.

9 Claims, 11 Drawing Sheets

U.S. PATENT DOCUMENTS

| | | |
|---|---|---|
| 3,981,031 | 9/1976 | Schacht . |
| 4,222,131 | 9/1980 | Holdt et al. . |
| 4,247,091 | 1/1981 | Glowacki et al. . |
| 4,346,487 | 8/1982 | Holdt et al. . |
| 4,390,011 | 6/1983 | Evans . |
| 4,489,449 | 12/1984 | Failor et al. . |
| 4,506,872 * | 3/1985 | Westerberg et al. ............. 5/622 X |
| 4,669,136 | 6/1987 | Waters et al. . |
| 4,751,755 | 6/1988 | Carey et al. . |
| 4,881,728 | 11/1989 | Hunter . |
| 4,882,797 | 11/1989 | Failor et al. . |
| 4,974,903 * | 12/1990 | Lipschitz et al. ............. 297/188 |
| 5,135,210 | 8/1992 | Michelson . |
| 5,233,713 * | 8/1993 | Murphy et al. ............. 5/622 X |
| 5,335,384 | 8/1994 | Foster et al. . |
| 5,347,668 | 9/1994 | Manning . |
| 5,427,436 * | 6/1995 | Lloyd ............................ 5/622 X |
| 5,481,770 | 1/1996 | Ahlsten . |
| 5,575,026 | 11/1996 | Way et al. . |
| 5,675,851 | 10/1997 | Feathers . |
| 5,699,567 | 12/1997 | Sanders et al. . |
| 5,926,876 | 6/1999 | Haigh et al. . |

OTHER PUBLICATIONS

Models 878, 678 & 675, Uni–Care Mobile Surgical Stretchers, p. 14, date unknown.

Stryker Patient Handling, "Head & Neck Surgery Stretcher Model 1068", 5 pages, Oct. 1994.

Stryker Patient Handling, "Head & Neck Surgery Stretcher Model 1068", 6 pages, Sep. 1993.

Stryker Patient Handling, "Extended Stay Stretcher Model 1550", 5 pages, Sep. 1993.

* cited by examiner

ADJUSTABLE HEAD REST FOR A PATIENT SUPPORT

This application is a divisional of U.S. application Ser. No. 08/892,147, filed Jul. 14, 1997 now U.S. Pat. No. 6,076,208.

BACKGROUND AND SUMMARY OF THE INVENTION

The present invention relates to a hospital stretcher, and particularly, to a surgical stretcher used for head and neck surgery. More particularly, the present invention relates to a surgical stretcher having a head rest that is adjustable relative to a back section of the stretcher and having hardware, such as a wrist rest assembly and extender board assemblies, that are used in conjunction with the head rest.

Hospital stretchers having head rests that support the head of a patient during head and neck surgery are known. See, for example, U.S. Pat. No. 4,882,797 to Failor et al. Hospital stretchers having wrist rests that support the wrists of a surgeon performing surgery on the head and neck of the patient are also known. See, for example, the Failor et al. '797 patent and U.S. Pat. No. 4,390,011 to Evans.

Some head rests are adjustable so that the surgeon can move the head of the patient to a desired position and some wrist rests are adjustable so that the surgeon can move the wrist rest to a desired position relative to the head of the patient. See, for example the Failor et al. '797 patent which shows a knob at a foot end of the stretcher that can be rotated to rotate a plurality of hollow and slotted connecting tubes, an extension shaft, an adjustment rod, a plurality of universal joints, and a slide shaft, all of which operate through a worm gear reducer to adjust the position of a head support plate which is situated at a head end of the stretcher. The Failor et al. '797 patent also shows an adjustable wrist rest assembly having a longitudinally-extending square tube which fits into a slightly larger longitudinally-extending square tube that is centrally positioned with respect to sides of the head support plate and that is welded to the bottom of a main support plate connected to the head support plate.

Head rests on stretchers used for head and neck surgery typically have smaller widths than the rest of the surface which supports the patient to facilitate access to the head of the patient by the surgeon. Some stretchers having head rests may include extension assemblies that mount to the stretcher adjacent to the head rest to increase the overall width of the support surface in the vicinity of the head and shoulders of the patient. See, for example, the Failor et al. '797 patent which shows a head rest extension assembly that mounts directly to the head rest. The head rest extension assembly of the Failor et al. '797 patent includes a U-shaped plate and a longitudinally-extending square tube that can fit within the centrally positioned tube mounted to the main support plate when the wrist rest assembly is removed from the centrally positioned tube. See also, the Stryker Model 1068 Head and Neck Surgery Stretcher advertising literature which shows a pair of padded head extensions that rigidly attach to a litter of the stretcher and that remain at a single position adjacent to a head piece while attached to the litter.

Arm boards that can be coupled to the sides of a stretcher and arranged to support the arms of the patient are known. See, for example, U.S. Pat. No. 2,972,505 to Weickgenannt. Some arm boards can pivot relative to the stretcher so that an arm of the patient can be moved to a desired position, for example, to receive IV fluids.

Stretchers having foot pedals that can be engaged to actuate a center wheel mechanism and braking mechanisms of the stretcher are also known in the art. Stretchers having a head rest may include such foot pedals beneath the head rest. See, for example, the Failor et al. '797 patent and the Stryker Model 1068 Head and Neck Surgery Stretcher advertising literature. Sometimes these foot pedals can get in the way of foot-operated surgical equipment that the surgeon uses during head and neck surgery.

What is needed is a surgical stretcher having a head rest that can be easily adjusted relative to a back section of the stretcher by a caregiver or surgeon while standing at a head end of the stretcher. The stretcher should include an adjustable wrist rest assembly that can attach to and detach from the head rest. The stretcher should also include a pair of extender boards that can couple to sides of the back section and pivot between a first position in which the extender boards function as head rest extenders and a second position in which the extender boards function as arm boards. In addition, the position of the back section of the stretcher should be manually adjustable when the extender boards are in either the first or second positions. A stretcher having a foot pedal that can be moved to an out-of-the-way position to prevent interference of the foot pedal with foot-operated surgical equipment would provide many advantages to surgeons as well.

According to the present invention, a surgical stretcher is provided including a frame and a patient-support deck coupled to the frame. A head rest is coupled to the patient-support deck. The head rest includes a pair of longitudinally-extending spaced-apart socket tubes and a bottom plate extending transversely between the socket tubes. A side plate angles upwardly from each of the socket tubes so that a head cushion-receiving space is defined between the side plates. Each of the socket tubes has an interior region and each socket tube is open so that portions of a wrist rest assembly can be inserted into the interior region of the socket tubes.

A wrist rest assembly includes a first rod that can be received in the interior region of one of the pair of socket tubes and a second rod that can be received in the interior region of the other of the pair of socket tubes. The wrist rest assembly includes an end tube coupled to the first rod and a knob mounted on the second tube and coupled to the end tube. The knob can be rotated in a first direction to bind the first and second rods against respective socket tubes to prevent movement of the first and second rods relative to the head rest and the knob can be rotated in a second direction to unbind the first and second rods from respective socket tubes to allow movement of the first and second rods relative to the head rest.

The stretcher includes a bracket that couples the head rest to the back section. The bracket is coupled to the patient-support deck for pivoting movement about a transverse first pivot axis. The head rest is coupled to the bracket for pivoting movement about a transverse second pivot axis. A grip handle is coupled to the head rest and the grip handle has a side handle portion extending alongside the head rest in spaced-apart relation therewith so that the grip handle can be grasped to control pivoting movement of the head rest and bracket relative to the patient-support deck.

The stretcher includes a first locking mechanism that locks the bracket relative to the back section and a second locking mechanism that locks the head rest relative to the bracket. A release button is coupled to the first and second locking mechanisms. The release button can be pressed to simultaneously unlock the first and second locking mechanisms so that the head rest can be manually repositioned relative to the back section and relative to the bracket. The release button is positioned to lie between the side handle portion of the grip handle and the head rest so that the release button can be pressed while the side handle portion of the grip handle is grasped.

The patient-support deck includes a back section coupled to the frame for pivoting movement about a transverse pivot axis. The back section has first and second longitudinal sides and a transverse end extending between the sides. In addition, the back section has a substantially planar back-support surface. An extender board having an extension surface substantially coplanar with the back-support surface can be coupled to each side of the back section for pivoting movement relative to the back section.

An actuator couples the back section to the frame of the stretcher. The actuator is lockable to prevent pivoting movement of the back section relative to the frame and the actuator is releasable to allow pivoting movement of the back section relative to the frame. A first releasing assembly is coupled to the back section and coupled to the actuator. Actuation of the first releasing assembly releases the actuator so that the back section can be manually pivoted relative to the frame.

The back section includes a pair of corner portions that can be grasped to manually move the back section when the actuator is released. The first release assembly includes a pair of handle portions, each of which are adjacent to respective corner portions of the back section. One or the other of the handle portions and companion corner portions can be grasped at the same time and the handle portion can be squeezed toward the corner portion to release the actuator.

A second releasing assembly is coupled to the extender board. The extender board has a first position in which actuation of the second releasing assembly actuates the first releasing assembly to release the actuator so that the back section can be manually pivoted relative to the frame.

The extender board is connected to the back section by a connector assembly that is configured to allow a corner portion of the extender board to be grasped to manually move the back section when the extender board is in the first position and the actuator is released. The second releasing assembly includes a handle portion which is adjacent to the corner portion of the extender board. The handle portion of the second releasing assembly and the corner portion of the extender board can be grasped at the same time and the handle portion of the second actuator can be squeezed toward the corner portion of the extender board to release the actuator when the extender board is in the first position.

The patient-support apparatus also includes a pedal assembly for rotating a brake-steer shaft of the patient-support apparatus about an axis. The pedal assembly includes a yoke coupled to the brake-steer shaft to rotate therewith. The pedal assembly also includes a flip-over pedal having a proximal end coupled to the yoke and a distal end spaced apart from the proximal end. The flip-over pedal is pivotable about a flip-over axis relative to the yoke. The flip-over pedal has a first orientation in which the flip-over pedal extends away from the yoke in a first direction so that the distal end of the flip-over pedal can be engaged to rotate the brake-steer shaft in a first direction. The flip-over pedal has a second orientation in which the flip-over pedal extends away from the yoke in a second direction so that the distal end of the flip-over pedal can be engaged to rotate the brake-steer shaft in a second direction opposite to the first direction.

Additional objects, features, and advantages of the invention will become apparent to those skilled in the art upon consideration of the following detailed description of a preferred embodiment exemplifying the best mode of carrying out the invention as presently perceived.

BRIEF DESCRIPTION OF THE DRAWINGS

The detailed description particularly refers to the accompanying figures in which.

DETAILED DESCRIPTION OF THE DRAWINGS

Figure 1:
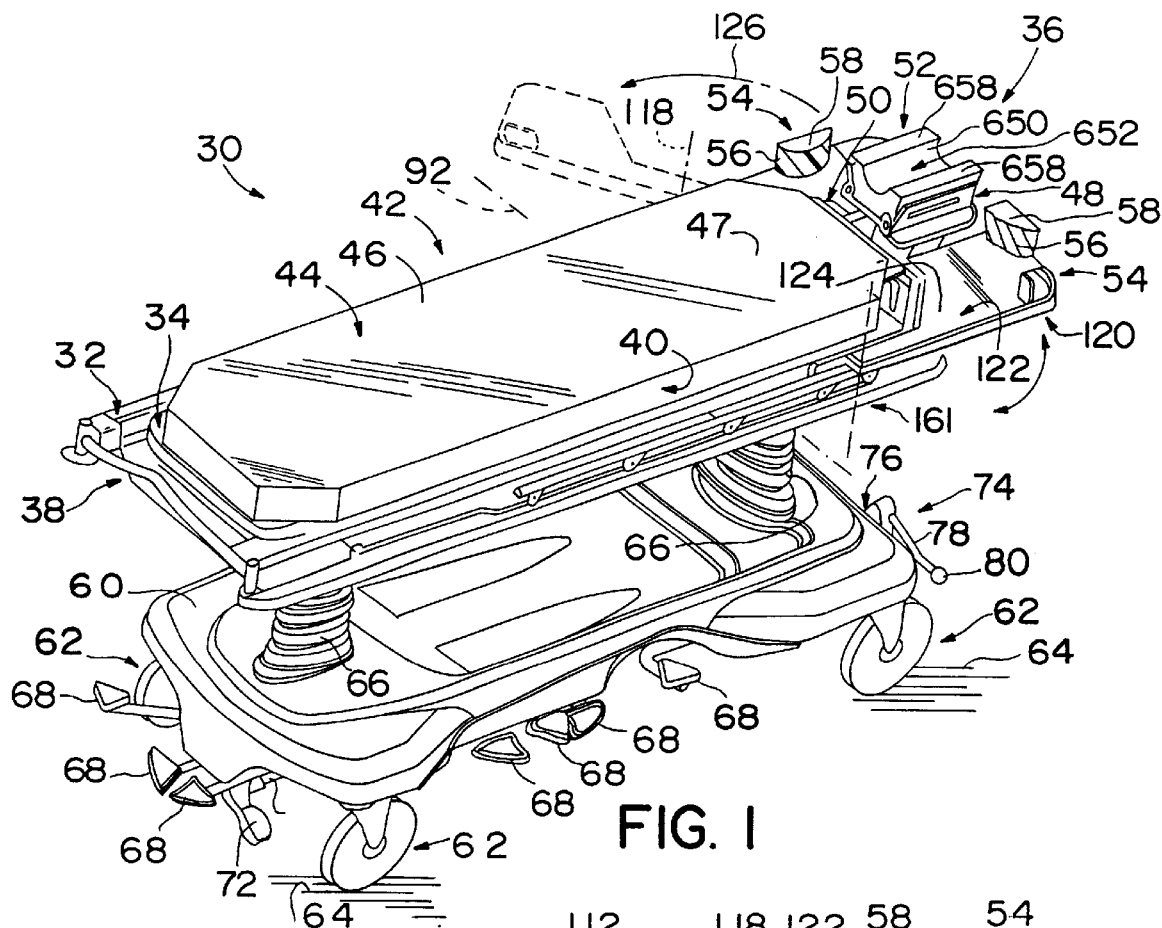
FIG. 1 is a perspective of a surgical stretcher in accordance with the present invention showing a patient support deck having a head end and a foot end, a head rest coupled to the head end of the patient-support deck, and extender boards mounted to sides of the patient-support deck, each of the extender boards being pivotable between a first position adjacent to the head rest and a second position extending toward the foot end of the patient-support deck.

A surgical stretcher 30 in accordance with the present invention includes a frame 32 and a patient-support deck 34 supported by frame 32 as shown in FIG. 1. Patient-support deck 34 has a head end 36, a foot end 38, and first and second longitudinal sides 40, 42 extending between head end 36 and foot end 38. Stretcher 30 includes a mattress 44 supported by patient-support deck 34. Mattress 44 has an upwardly-facing patient-support surface 46 on which a patient can rest.

Stretcher 30 includes a head rest 48 adjacent to head end 36 of patient-support deck 34. Head rest 48 is coupled to a back section 50 of patient-support deck 34 and the position of head rest 48 can be adjusted relative to back section 50. In addition, the position of back section 50 can be adjusted relative to frame 32 and relative to the rest of patient-support deck 34. Head rest 48 includes a head cushion 52 that supports the head of the patient.

Figure 2:
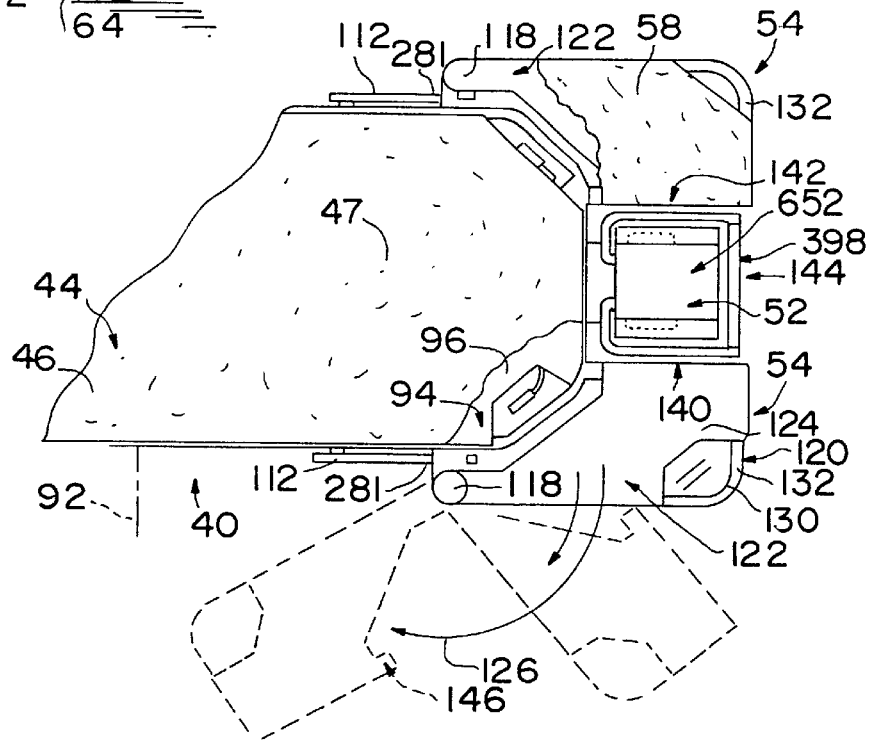
FIG. 2 is top plan view of the surgical stretcher of FIG. 1 showing both extender boards in their respective first positions adjacent to the head rest and showing one of the extenders pivoting through a transition position (in phantom) into the second position (in phantom) to function as an arm board.

Stretcher 30 also includes a pair of extender boards 54, each of which is mounted to respective first and second longitudinal sides 40, 42 of back section 50 of patient-support deck 34. Each extender board 54 supports a cushion 56 having an extension surface 58. Extender boards 54 are independently pivotable relative to back section 50 between a first position adjacent to head rest 48, as shown in FIGS. 1 and 2, and a second position extending away from back section 50 toward foot end 38 of patient-support deck 34, as shown in FIGS. 1 and 2 (in phantom). Stretcher 30 includes a pair of side guard assemblies 61 that, when moved to a lowered position as shown in FIG. 1, permit full movement of extender boards 54 between the first and second positions.

Stretcher 30 includes a lower frame (not shown) covered by a shroud 60 as shown in FIG. 1. Casters 62 are mounted to the lower frame and extend downwardly therefrom to engage a floor 64 on which stretcher 30 sets. Frame 32 and patient-support deck 34 are supported above the lower frame and shroud 60 by a pair of longitudinally spaced-apart elevation mechanisms (not shown), well-known to those skilled in the art. The elevation mechanisms are each covered by a boot 66 as shown in FIG. 1. Stretcher 30 includes a plurality of foot pedals 68 that are coupled to the elevation mechanisms. Different foot pedals 68 can be depressed so that the elevation mechanisms are actuated to raise, lower, or tilt frame 32 and patient-support deck 34 relative to floor 64.

Stretcher 30 also includes a longitudinally-extending brake-steer shaft 70. Brake-steer shaft 70 is coupled to a conventional caster braking mechanism 71 which is shown diagrammatically in FIG. 20 and which is well known to those skilled in the art. Caster braking mechanism 71 brakes casters 62 to prevent them from rotating and swivelling when brake-steer shaft 70 is rotated to a braking position. Brake-steer shaft 70 is also coupled to a conventional center wheel mechanism 73 which is also shown diagrammatically in FIG. 20 and which is also well known to those skilled in the art. Center wheel mechanism 73 lowers a center wheel (not shown) into engagement with floor 64 when brake-steer shaft 70 is rotated to a steering position.

A brake pedal 72 is coupled to brake-steer shaft 70 beneath foot end 38 of patient-support deck 34 and a pedal assembly 74 is coupled to brake-steer shaft 70 beneath head end 36 of patient-support deck 34. Brake pedal 72 can be engaged to rotate brake-steer shaft 70 to the braking position, thereby braking casters 62. Pedal assembly 74 includes a yoke 76 and a flip-over pedal 78 coupled to yoke 76 for pivoting movement. Flip-over pedal 78 is movable relative to yoke 76 between a first orientation in which a distal end portion 80 can be engaged to rotate brake-steer shaft 70 to the steering position and a second orientation in which end portion 80 can be engaged to rotate brake-steer shaft 70 to the braking position as will be discussed in detail below with reference to FIGS. 20–23.

Stretcher 30 is well suited for head and neck surgery, and particularly, for outpatient head and neck surgery. Prior to surgery, when the patient is resting on stretcher 30 in a pre-op waiting area, for example, extender boards 54 can be moved to the first position adjacent to head rest 48 so that extension surfaces 58 cooperate with patient-support surface 46 to increase the support surface area near the head and shoulders of the patient. Stretcher 30 can be used to transport the patient from the pre-op waiting area to an operating room where surgery is to be performed on the patient.

During transport, back section 50 can be placed in a desired position depending upon the preference of the caregiver or the patient. For example, if the patient is unconscious, back section 50 can be moved to a horizontal position in which the patient is supported in a lying-down position. Alternatively, if the patient is conscious and capable of sitting up, back section 50 can be moved to an inclined position in which back section 50 is angled at about seventy degrees (70°) relative to frame 32, thereby placing the patient in a sitting-up position. In addition, back section 50 can be moved to any one of an infinite number of intermediate positions between the horizontal and inclined positions, if desired.

During transport of the patient to the operating room, pedal assembly 74 can be used to move brake-steer shaft 70 to the steering position having the center wheel engaging floor 64 to assist in steering stretcher 30 by providing a frictional contact area with floor 64 about which stretcher 30 can be easily turned. After stretcher 30 reaches the desired location in the operating room, pedal assembly 74 can be used to move brake-steer shaft 70 to the braking position so that casters 62 are prevented from rotating or swivelling, thereby preventing stretcher 30 from moving along floor 64.

Prior to surgery, back section 50 can be moved to the horizontal position and one or both of extender boards 54 can be moved away from head rest 48 to their respective second positions. Placing each extender board 54 in the second position results in increased access to the head of the patient by the surgeon. In addition, extension surfaces 58 of cushions 56 can support the arms of the patient out past sides 40, 42 of patient-support deck 34 so that IV fluids and anesthesia can be administered to the patient during surgery. After the patient has been anesthetized, the surgeon can move the head of the patient to a desired surgical position by adjusting the position of head rest 48.

After surgery, extender boards 54 can be returned to their first positions adjacent to head rest 48. Pedal assembly 74 can be used to move brake-steer shaft 70 out of the braking position and into the steering position and stretcher 30 can then be used to transport the patient to a post-op area where the patient can recover from surgery. Thus, the patient can rest upon patient-support surface 46 of stretcher 30 before, during, and after surgery. In addition, extender boards 54 can be moved between first and second positions to function as head extenders and arm boards, respectively.

Figure 3:
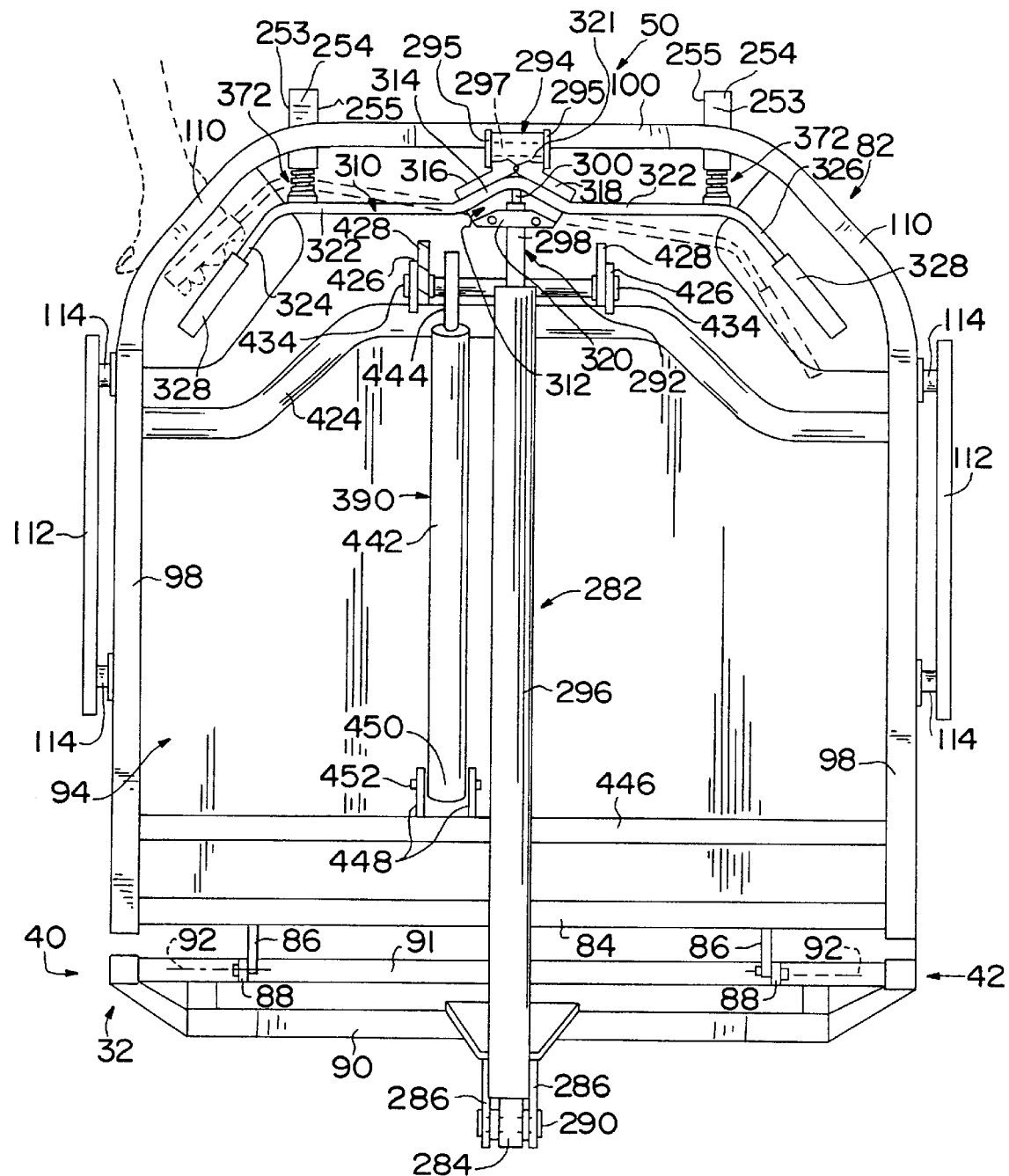
FIG. 3 is a rear elevation view of a back section of the patient-support deck of the stretcher of FIG. 1 in a substantially vertical position showing the back section having a tubular frame member defining the outer perimeter of the back section and a first releasing assembly coupled to the back section, the first releasing assembly being actuatable to unlock the back section for pivoting movement relative to a frame of the stretcher.

As previously described, back section 50 can be moved between horizontal and inclined positions. Back section 50 includes a tubular frame member 82 having a base strut 84 as shown in FIG. 3. A pair of transversely spaced-apart flanges 86 extend away from base strut 84 and couple to respective longitudinally-extending flanges 88 appended to a cross strut 91 of frame 32. Flanges 86 are pinned to flanges 88 so that back section 50 can pivot relative to frame 32 about a transverse pivot axis 92, shown, for example, in FIGS. 1–3.

Back section 50 includes a panel 94 attached to frame member 82. Panel 94 of back section 50 includes a substantially planar surface 96 that supports part of mattress 44 as shown in FIG. 2. The part of mattress 44 supported by surface 96 of panel 94 includes a back-support surface 47 that engages the upper torso of the patient resting on mattress 44.

Frame member 82 includes a pair of spaced-apart longitudinal side struts 98, a transverse end strut 100, and a pair of angled corner portions 110 connecting side struts 98 to end strut 100 as shown best in FIG. 3. Side struts 98, end strut 100, and angled corner portions 110 are configured so as to define a plane in which back section 50 is situated. A rail 112 is coupled to each side strut 98 by a pair of spacers 114 that position rails 112 in spaced-apart relation with respective side struts 98.

A connector assembly 116 is appended to each extender board 54. Connector assemblies 116 can be attached to rails 112, thereby coupling extender boards 54 to back section 50. When coupled to back section 50, extender boards 54 can pivot about a respective pivot axis 118 as shown in FIGS. 1 and 2. Each pivot axis 118 is substantially perpendicular to surface 96 of panel 94 of back section 50.

Each extender board 54 includes a frame 120 and a panel 122 attached to frame 120. Panel 122 of each extender board 54 includes a top surface 124 that supports cushion 56. As extender boards 54 pivot relative to back section 50, for example, in a direction 126 shown in FIGS. 1 and 2, surfaces 124 of panels 122 are maintained in substantially coplanar relation with surface 96 of panel 94 and extension surfaces 58 of cushions 56 are maintained in substantially coplanar relation with back-support surface 47 of mattress 44.

Figure 4:
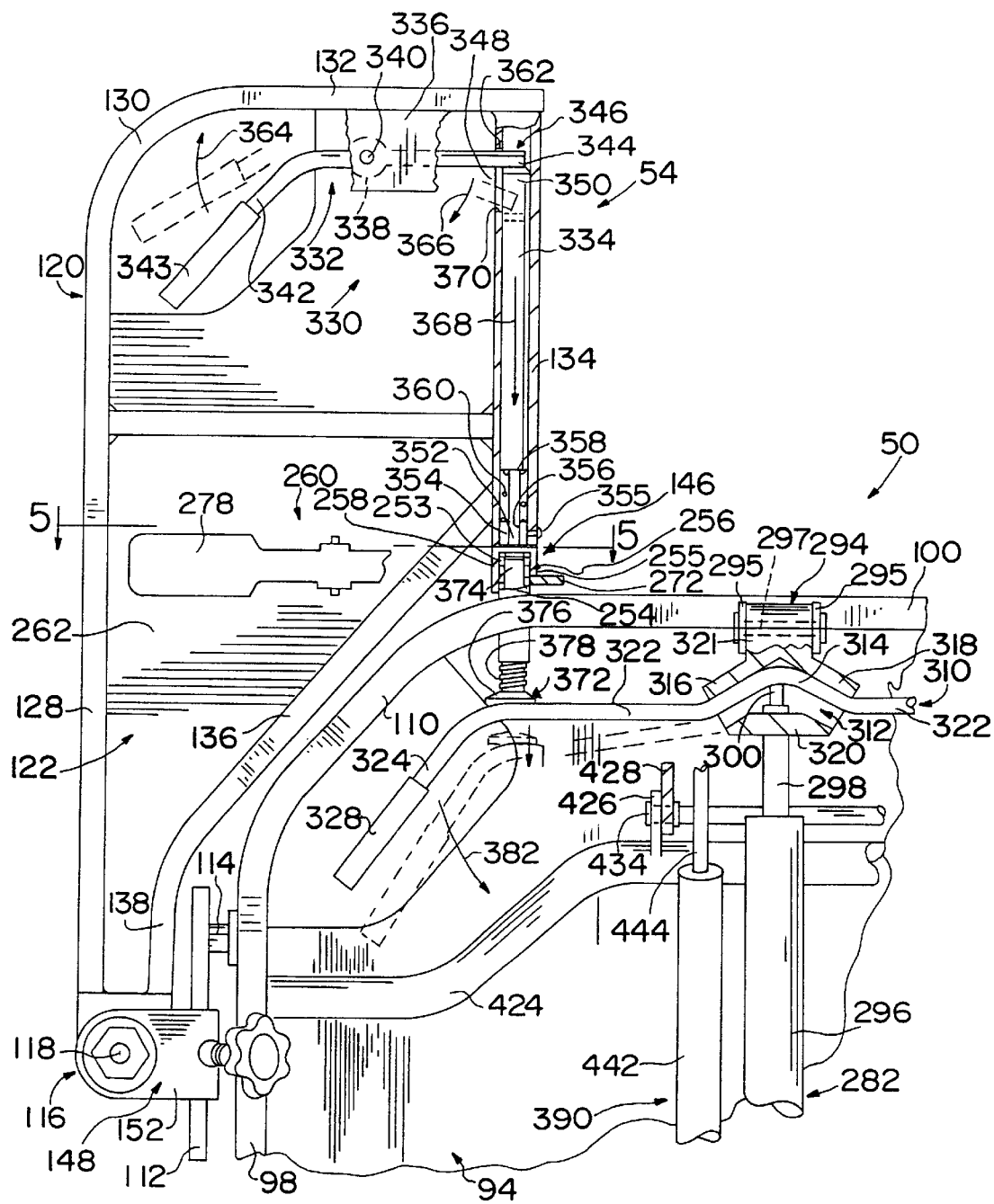
FIG. 4 is a view of the back section similar to FIG. 3, with portions broken away, showing one of the extender boards in the first position and a second releasing assembly coupled to the extender board, the second releasing assembly being actuatable to unlock the back section for pivoting movement relative to the frame of the stretcher.

Frame 120 of each extender board 54 includes a long side portion 128, a corner portion 130 integrally appended to portion 128, a distal end portion 132 integrally appended to corner portion 130 in perpendicular relation to portion 128, a mid-size side portion 134 appended to portion 132 in parallel relation with portion 128, an angled portion 136 extending away from portion 134 toward portion 128, and a short side portion 138 integrally appended to portion 136 in parallel relation with portion 128 as shown best in FIG. 4. Portions 128, 130, 132, 134, 136, 138 of frame 120 define the perimeter of extender boards 54. Panels 122 extend between portions 128, 130, 132, 134, 136, 138 of respective frames 120.

Head rest 48 has first and second longitudinally-extending sides 140, 142 and an end 144 connecting sides 140, 142. Sides 140, 142 of head rest 48 are spaced apart by a distance that is smaller than a distance by which sides 40, 42 of patient-support deck 34 are spaced apart. When extender boards 54 are in their first positions, mid-size side portions 134 of frames 120 are adjacent to the respective side 140, 142 of head rest 48, angled portions 136 of frames 120 are adjacent to the respective corner portion 110 of frame member 82, and short side portions 138 of frames 120 are adjacent to the respective side struts 98 of frame member 82. In addition, mid-size side portion 134 of each frame 120 includes a docking portion 146 that extends toward and is adjacent to end strut 100 of frame member 82 of back section 50 when the respective extender board 54 is in the first position.

When extender boards 54 are in their first positions, distal end portions 132 of each frame 120 extend substantially transversely and are generally aligned with end 144 of head rest 48 as shown in FIG. 2. In addition, when extender boards 54 are in their first positions, side portions 128, 134, and 138 are all substantially parallel with side struts 98 of frame member 82 of back section 50. Thus, when extender boards 54 are in their first positions adjacent to head rest 48, extension surfaces 58 provide additional surface area on which the head and shoulders of the patient can rest.

Each extender board 54 can pivot about respective axes 118 from the first position to a second position in which portion 134 of frame 120 is no longer adjacent to the respective side 140, 142 of head rest 48. Extender boards 54 extend more toward foot end 38 of patient-support deck 34 than head end 36 of patient-support deck 34 when in the second position, as shown in FIGS. 1 and 2. Thus, when extender boards 54 are in their second positions, extension surfaces 58 can support the arms of the patient out past sides 40, 42 of patient-support deck 34.

As previously described, connector assemblies 116 couple each extender board 54 to a companion rail 112 and allow each extender board 54 to pivot about a respective axis 118. The description below of one of the connector assemblies 116 applies to the other of the connector assemblies 116 as well.

Figure 6:
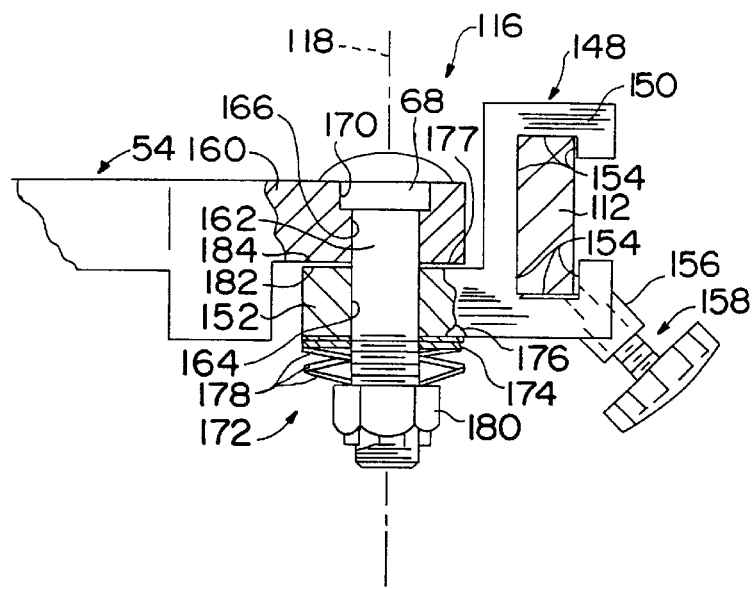
FIG. 6 is a sectional view of a first embodiment connector assembly that connects each of the extender boards to one of a pair of rails attached to the back section frame member showing the connector assembly including two clutch disks overlying a clutch assembly that biases the clutch disks together in frictional engagement with one another.

Connector assembly 116 includes a slide block 148 having a rail-engaging portion 150 and a clutch plate 152 extending away from rail-engaging portion 150 as shown in FIG. 6. Rail-engaging portion 150 of slide block 148 is generally C-shaped so as to define a channel 154 that receives rail 112. Channel 154 of portion 150 is formed to allow longitudinal sliding movement of connector assembly 116 and the associated extender board 54 relative to rail 112.

Connector assembly 116 includes a threaded cylinder 156 appended to a bottom corner portion of rail-engaging portion 150. A turn screw 158 is threadedly coupled to cylinder 156. Turn screw 158 can be turned to tighten slide block 148 against rail 112 to prevent connector assembly 116 from sliding relative to rail 112. Turn screw 158 can also be turned to loosen slide block 148 from rail 112 to allow connector assembly 116 to slide relative to rail 112. Thus, connector assembly 116 and extender board 54 can be moved to a desired position along rail 112 and then turn screw 158 can be turned to lock connector assembly 116 at the desired position.

Clutch plate 152 extends horizontally away from its companion rail-engaging portion 150 as shown in FIG. 6. A second clutch plate 160 of connector assembly 116 is attached to extender board 54 and is supported by clutch plate 152. In addition, clutch plate 160 is connected to clutch plate 152 by a bolt 162 that extends through apertures 164, 166 formed in clutch plates 152, 160, respectively.

As extender board 54 pivots about axis 118, clutch plate 160 pivots relative to clutch plate 152. Bolt 162 includes a square-shaped lug 168 and clutch plate 160 includes a square-shaped recess 170 that receives lug 168 so that bolt 162 turns along with clutch plate 160 as clutch plate 160 is turned relative to clutch plate 152. Bolt 162 cooperates with apertures 164, 166 of plates 152, 160 to define pivot axis 118.

Bolt 162 extends downwardly past clutch plate 152 and a clutch assembly 172 is mounted to the downwardly-extending portion of bolt 162 as shown in FIG. 6. Clutch assembly 172 includes a lower self-lubricating washer 176, a flat washer 174, and a set of three Belleville washers 178 that bias flat washer 174 against lower self-lubricating washer 176. A nut 180 threadedly engages bolt 162 so that clutch plates 152, 160 and clutch assembly 172 are clamped together, thereby loading washers 178. An upper self-lubricating washer 177 is sandwiched between clutch plates 152, 160. The loading of washers 178 causes a top surface 182 of clutch plate 152 and a bottom surface 184 of clutch plate 160 to engage upper self-lubricating washer 177 with sufficient force to hold extender board 54 at any desired position between the first and second positions, independent of the position of back section 50, while also allowing extender board 54 to be manually moved about axis 118 from one position to another. Upper and lower self-lubricating washers 176, 177 can be, for example, oil-impregnated brass bushings supplied by OILITE™.

Figure 7:
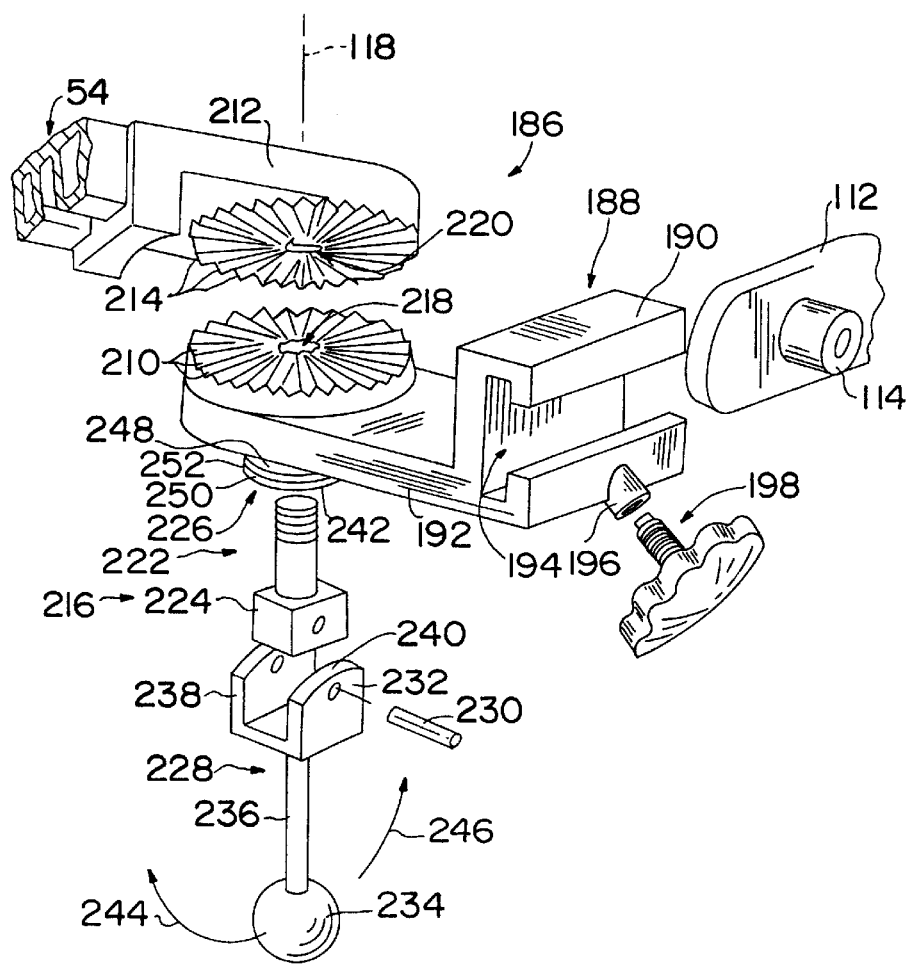
FIG. 7 is an exploded perspective view of a second embodiment connector assembly that connects each of the extender boards to the respective rail showing the second embodiment connector assembly including two toothed clutch disks overlying an assembly for clamping the clutch disks together.

An alternative embodiment connector assembly 186 is shown in FIG. 7. The description below of one of the connector assemblies 186 applies to the other of connector assemblies 186 as well. Connector assembly 186 includes a slide block 188 having a rail-engaging portion 190 and a plate 192 extending away from rail-engaging portion 190 as shown in FIG. 6. Rail-engaging portion 190 of slide block 188 is generally C-shaped so as to define a channel 194 that receives rail 112. Channel 194 of portion 190 is formed to allow longitudinal sliding movement of connector assembly 186 and the associated extender board 54 relative to rail 112.

Connector assembly 186 includes a threaded cylinder 196 appended to a bottom corner portion of rail-engaging portion 190 and a turn screw 198 threadedly coupled to cylinder 196. Turn screw 198 of connector assembly 186 operates to prevent and allow sliding movement of connector assembly 186 relative to rail 112 in a manner similar to the manner in which turn screw 158 of connector assembly 116 operates to prevent and allow sliding movement of connector assembly 116 relative to rail 112.

A plurality of radially-extending upwardly-projecting teeth 210 is appended to plate 192 as shown in FIG. 7. Connector assembly 186 includes a second plate 212 attached to extender board 54. A plurality of radially-extending downwardly-projecting teeth 214 is appended to plate 212. Connector assembly 186 includes a clamping assembly 216 that is movable between a locking position, in which teeth 210 mesh with teeth 214 to prevent pivoting movement of extender board 54 about pivot axis 118, and a releasing position, in which teeth 210 do not mesh with teeth 214 to allow pivoting movement of extender board 54 about axis 118.

Plate 192 is formed to include an aperture 218 and plate 212 is formed to include a threaded aperture 220 as shown in FIG. 7. Clamping assembly 216 includes a bolt 222 having an end portion received by aperture 220 and threadedly coupled to plate 212 so that bolt 222 rotates along with clutch plate 212 as clutch plate 212 pivots about axis 118 relative to clutch plate 192. Bolt 222 also includes a portion received by aperture 218 for rotating movement. Bolt 222 cooperates with apertures 218, 220 of plates 192, 212 to define pivot axis 118.

Bolt 222 includes a block portion 224 positioned to lie underneath plate 192 as shown in FIG. 7. Connector assembly 186 includes a cylindrical spacer subassembly 226 between block portion 224 and plate 192. In addition, connector assembly 186 includes a lever 228 having a yoke 232, a knob 234, and a rod 236 connecting yoke 232 to knob 234. Yoke 232 of lever 228 is coupled to block portion 224 of bolt 222 by a pivot pin 230 so that lever 228 can pivot relative to bolt 222 and plate 192. Yoke 232 includes a pair of spaced-apart U-shaped locking edges 238 and a pair of curved edges 240 as shown in FIG. 7.

Lever 228 can be moved to a vertical releasing position in which curved surfaces 240 face substantially upwardly toward a bottom surface 242 of spacer subassembly 226 as shown in FIG. 7. When lever 228 is in the releasing position, extender board 54 can be lifted upwardly by a slight amount so that teeth 210 of plate 192 do not mesh with teeth 214 of plate 212 and then extender board 54 can be pivoted about axis 118 relative to back section 50. Thus, when lever 228 in the releasing position, connector assembly 186 is in the releasing position and the position of extender board 54 can be adjusted.

Lever 228 can pivot from the releasing position in a first direction indicated by arrow 244, shown in FIG. 7, to a first locking position in which one of locking edges 238 abuts bottom surface 242 of spacer subassembly 226. Lever 228 can also pivot from the releasing position in a second direction indicated by arrow 246, shown in FIG. 7, to a second locking position in which the other one of locking edges 238 abuts bottom surface 242 of spacer subassembly 226. When lever 228 is in either the first locking position or the second locking position, plate 212 is clamped against plate 192 so that teeth 210 mesh with teeth 214, thereby preventing extender board 54 from pivoting relative to back section 50. Thus, when lever 228 is in either the first or the second locking position, connector assembly 186 is in the locking position and extender board 54 is locked in place relative to back section 50.

Spacer subassembly 226 includes a cylinder 248 beneath clutch plate 192, a washer 250 beneath cylinder 248, and a hard rubber washer 252 sandwiched between washer 250 and cylinder 248. As lever 228 is moved between the releasing position and either of the first or second locking positions, rubber washer 252 is compressed as washer 250 is forced toward cylinder 252 by lever 228. When lever 228 is in either the first or the second locking position, rubber washer 252 is held in compression so that washer 250 acts through lever 228 and bolt 222 to bias plate 212 against plate 192. The compression of rubber washer 252 also biases washer 250 against one or the other of edges 238 of yoke 232. Biasing of one of edges 238 with washer 250 holds lever 228 in the respective first or second locking position.

As previously described, frame 120 of each extender board 54 includes a docking portion 146. Stretcher 30 includes a pair of posts 254 coupled to end strut 100 of frame member 82 of back section 50. Posts 254 extend longitudinally away from end strut 100 as shown, for example, in FIG. 3. Each docking portion 146 is essentially a square-shaped tube having a window 256 cut out of one of the sides so that posts 254 can be received inside docking portions 146. When extender boards 54 are pivoted into their first positions, posts 254 pass through windows 256 so that a side wall 258 of each docking portion 146 can engage a first side 253 of respective posts 254 to locate extender boards 54 in their first positions.

Figure 5:
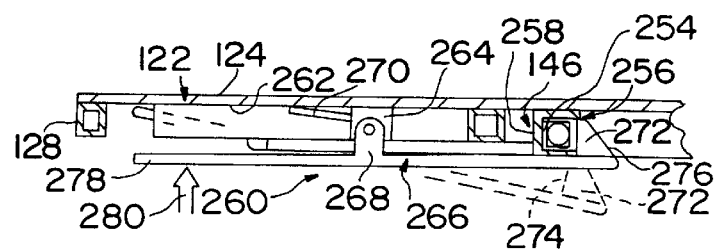
FIG. 5 is a sectional view taken along line 5—5 of FIG. 4 showing a latch mounted to the extender board for movement between a locking position in which the extender board is locked in the first position and a releasing position (in phantom) in which the extender board is unlocked and can pivot relative to the back section.

If extender boards 54 are coupled to back section 50 by connector assemblies 116, stretcher 30 can include a latch assembly 260 coupled to an undersurface 262 of panel 122 of extender boards 54 as shown in FIGS. 4 and 5. The description below of one of latch assemblies 260 is descriptive of both latch assemblies 260.

Latch assembly 260 includes a bracket 264 that attaches to undersurface 262 of panel 122 and a latch plate 266 having a pair of central flanges 268 pinned to bracket 264. Latch assembly 260 also includes a torsion spring 270 that engages undersurface 262 of panel 122 and latch plate 266 to bias latch plate 266 into a locking position as shown in FIG. 5.

Latch plate 266 includes an upturned tab 272 having a locking edge 274 and a cam edge 276 as shown in FIG. 5. When latch plate 266 is in the locking position and extender board 54 is in the first position, locking edge 274 of tab 272 engages a second side 255 of post 254 so that extender board 54 is locked in the first position. Latch plate 266 includes a hand-engaging portion 278 adjacent to long side portion 128 of frame 120 as shown in FIG. 4. Hand-engaging portion 278 of latch plate 266 can be moved in a direction indicated by a double arrow 280, shown in FIG. 5, toward undersurface 262 of panel 122 to move latch plate 266 from the locking position to a releasing position, shown in FIG. 5 (in phantom). When latch plate 266 is in the releasing position, locking edge 274 is spaced apart from second side 255 of post 254 allowing extender board 54 to be moved out of the first position toward the second position.

When extender board 54 is moved from the second position back to the first position, cam edge 276 of tab 272 ramps against post 254 to automatically move latch plate 266 from the locking position to the releasing position allowing extender board 54 to be moved all the way into the first position. After extender board 54 reaches the first position having side wall 258 of docking portion 146 engaging first side 253 of post 254, torsion spring 270 urges latch plate 266 back into the locking position so that extender board 54 is locked in the first position. Thus, engagement of first side 253 of post 254 with side wall 258 of docking portion 146 prevents extender board 54 from pivoting past the first position toward head rest 48 and engagement of locking edge 274 of latch plate 266 prevents extender board 54 from pivoting out of the first position away from head rest 48.

A locator post 281 is coupled to and extends away from each of rails 112 as shown in FIG. 2. When each connector assembly 116 is mounted to the respective rail 112 by sliding rail-engaging portion 150 of slide block 148 onto rail 112 in a direction toward foot end 38 of patient-support deck 34, engagement of slide block 148 with post 281 places connector assembly 116 at the proper location so that docking portion 146 of frame 120 of extender board 54 will engage post 254 when extender board 54 is moved to the first position. Locator posts 281 serve this same function when extender boards 54 are coupled to rails 112 by connector assemblies 186 rather than connector assemblies 116. Rails 112 each have sufficient length to allow other medical equipment, such as IV poles, to be mounted to rails 112 even when extender boards are coupled to rails 112.

As previously described, back section 50 can pivot about axis 92 between horizontal and inclined positions and can be situated in an infinite number of intermediate positions between the horizontal and inclined positions. Stretcher 30 includes an actuator 282 having a first end 284 pivotably coupled to a pair of flanges 286 as shown in FIG. 3. Flanges 286 are coupled to cross strut 90 of frame 32 and first end 284 of actuator 282 is coupled to flanges 286 by a pin 290. Actuator 282 has a second end 292 coupled to a pivot block 294 which is pivotably coupled by a pin 297 to a pair of flanges 295 extending from end strut 100 of frame member 82 as shown in FIGS. 3 and 4. Actuator 282 is releasable so that back section 50 can pivot about axis 92 relative to frame 32 and actuator 282 is lockable so that back section 50 is prevented from pivoting about axis 92 relative to frame 32.

In a preferred embodiment, actuator 282 is a gas spring (hereinafter referred to as gas spring 282) although it is within the scope of the invention as presently perceived for actuator 282 to include any locking mechanism that can extend and retract and that can be locked to prevent movement of the actuator. Thus, the term "actuator" as used in this specification and in the claims includes a gas spring, a spring clutch, a ball screw, a hydraulic cylinder, a pneumatic cylinder, or any other suitable mechanism that can be locked to prevent back section 50 from pivoting relative to frame 32 and that can be released to allow back section 50 to be grabbed and manually pivoted relative to frame 32.

Gas spring 282 includes a housing 296, a piston (not shown) inside housing 296, and a piston rod 298 coupled to the piston and extending out of housing 296. Housing 296 is coupled to flanges 286 and piston rod 298 is coupled to pivot block 294. Gas spring 282 can be locked so that the piston and piston rod 298 are generally fixed relative to housing 296 so that piston rod 298 can neither extend further out of housing 296 nor retract into housing 296, thereby preventing back section 50 from pivoting about axis 92 relative to frame 32. Gas spring 282 can also be released so that the piston can move and piston rod 298 can extend and retract relative to housing 296, thereby allowing back section 50 to be grabbed and pivoted about axis 92 relative to frame 32.

Gas spring 282 includes a plunger 300 extending out of piston rod 298 as shown in FIGS. 3 and 4. Plunger 300 has an extended locking position in which gas spring 282 is locked preventing back section 50 from pivoting relative to frame 32. Plunger 300 also has a plunged releasing position in which gas spring 282 is released allowing back section 50 to pivot relative to frame 32. Plunger 300 is biased into the extended locking position so that gas spring 282 is normally locked.

Stretcher 30 includes a release rod 310 that can be actuated to move plunger 300 from the locking position to the releasing position. Pivot block 294 is formed to include a channel 312 and release rod 310 includes a middle portion 314 received within channel 312. Channel 312 extends generally transversely through pivot block 294 along a V-shaped path defined by first and second angled side walls 316, 318 and a bottom side wall 320 having chamfered corner portions. Middle portion 314 of release rod 310 is bent so that middle portion 314 is trapped within channel 312 by side walls 316, 318, 320 of pivot block 294, thereby preventing release rod 310 from moving transversely relative to back section 50. A plate 321 is attached to pivot block 294 to cover channel 312, thereby preventing release rod 310 from falling out of channel 312.

Release rod 310 includes straight portions 322 that extend transversely away from middle portion 314 beyond pivot block 294 toward respective first and second sides 40, 42 of back section 50. Release rod 310 also includes first and second handle portions 324, 326 that are each situated in the plane of back section 50 adjacent to respective corner portions 110 of frame member 82 as shown in FIG. 3. Handle portions 324, 326 angle away from straight portions 322 so that handle portions 324, 326 are generally parallel with corner portions 110 of frame member 82. A soft handle cover 328 is attached to each of handle portions 324, 326 to provide a comfortable feel to handle portions 324, 326.

Panel 94 is cut out in the region adjacent to corner portions 110 and handle portions 324, 326 to allow access to handle portions 324, 326 from above back section 50 and from below back section 50. Handle portions 324, 326 are in close proximity to respective corner portions 110 of frame member 82 so that the caregiver or the surgeon can simultaneously grasp one of corner portions 110 and one of handle portions 324, 326.

Handle portion 324 can be squeezed toward the adjacent corner portion 110 of frame member 82 to move plunger 300 from the locking position to the releasing position or, alternatively, handle portion 326 can be squeezed toward the adjacent corner portion 110 of frame member 82 to move plunger 300 from the locking position to the releasing position. Thus, release rod 310 and pivot block 294 cooperate to provide stretcher 30 with a releasing assembly that can be actuated to adjust the position of back section 50.

When handle portion 324 is squeezed toward the adjacent corner portion 110, release rod 310 pivots about a corner of first angled side wall 316 into a first releasing position as shown in FIG. 3 (in phantom). As release rod 310 moves toward the first releasing position, handle portion 326 moves away from the adjacent corner portion 110 and middle portion 314 separates away from second angled side wall 318 to move plunger 300 toward the releasing position.

Alternatively, when handle portion 326 is squeezed toward the adjacent corner portion 110, release rod 310 pivots about a corner of second angled side wall 318 into a second releasing position. As release rod 310 moves toward the second releasing position, handle portion 324 moves away from the adjacent corner portion 110 and middle portion 314 separates away from first angled side wall 316 to move plunger 300 toward the releasing position.

Thus, first angled side wall 316 has a corner that provides a first fulcrum point about which release rod 310 can pivot and second angled side wall 318 has a corner that provides a second fulcrum point about which release rod 310 can pivot, thereby allowing either of handle portions 324, 326 to be actuated to unlock back section 50 for pivoting movement relative to frame 32. In addition, the caregiver or surgeon can simultaneously grasp one of corner portions 110 of frame member 82 and the respective handle portion 324, 326 of release rod 310 so that after actuation of one of handle portions 324, 326, the caregiver or surgeon can manually pivot back section 50 relative to frame 32 of stretcher 30.

Another releasing assembly 330 is coupled to each extender board 54 so that when extender boards 54 are in the respective first positions, either releasing assembly 330 can be actuated to actuate release rod 310 which releases gas spring 282 allowing back section 50 to pivot relative to frame 32. The description below of one of releasing assemblies 330 is descriptive of both releasing assemblies.

Releasing assembly 330 includes a release lever 332 and a plunger rod 334 as shown in FIG. 4. A plate 336 is attached to distal end portion 132 and mid-size side portion 134 of frame 120 of extender board 54. Release lever 332 includes a middle portion 338 coupled to plate 336 by a pivot pin 340. Release lever 332 also includes an end 344 that engages plunger rod 334 and a handle portion 342 positioned to lie in close proximity to corner portion 130 of frame 120 so that corner portion 130 and handle portion 342 can be grasped simultaneously when releasing assembly 330 is actuated. A soft handle cover 343 is attached to handle portion 342 to provide a comfortable feel to handle portions 342.

Mid-size side portion 134 of frame 120 is formed to include an internal chamber 346 and plunger rod 334 is received in chamber 346 for sliding movement. In addition, mid-size side portion 134 of frame 120 is formed to include a slot 348 that provides access to chamber 346. Release lever 332 extends through slot 348 so that end 344 of release lever 332 is received in chamber 346.

Plunger rod 334 includes a first end 350 engaging end 344 of release lever 332 within chamber 346. Plunger rod 334 also includes a second end 352 spaced apart from first end 350 as shown in FIG. 4. Frame 120 includes an end block 354 coupled to mid-size side portion 134 by a screw 355. End block 354 is formed to include an aperture 356 and second end 352 of plunger rod 334 extends through aperture 356 into docking portion 146 of frame 120. Plunger rod 334 is formed to include a shoulder 358 and a coil spring 360 is positioned to lie between shoulder 358 and end block 354. Coil spring 360 is maintained in a state of compression so that plunger rod 334 is biased toward distal end portion 132 of frame 120 and into engagement with end 344 of release lever 332.

Mid-size side portion 134 of frame 120 includes an edge 362 that defines a first end of slot 348. When release lever 332 is unactuated, spring 360 acts through plunger rod 334 to bias release lever 332 into engagement with edge 362. Engagement of release lever 332 with edge 362 prevents plunger rod 334 from moving past the position shown in FIG. 4 toward distal end portion 132 of frame 120. When release lever 332 engages edge 362 releasing assembly 330 is in a locking position.

Movement of handle portion 342 of release lever 332 toward corner portion 130 of frame 120 in a direction indicated by arrow 364, shown in FIG. 4, causes end 344 of release lever 332 to move in a direction indicated by arrow 366. Movement of end 344 in direction 366 pushes plunger rod 334 in a direction indicated by arrow 368 resulting in second end 352 of plunger rod moving further into docking portion 146 of frame 120. In addition, movement of plunger rod 334 in direction 368 further compresses spring 360.

Portion 134 of frame 120 includes an edge 370 that defines a second end of slot 348. Handle portion 342 can be moved in direction 364 until release lever 332 engages edge 370. Engagement of release lever 332 with edge 370 prevents plunger rod 334 from moving past the position shown in FIG. 4 (in phantom). When release lever 332 engages edge 370 releasing assembly 330 is in a releasing position.

As previously described, when extender board 54 is in the first position, docking portion 146 engages post 254 to locate extender board 54 in the first position. In addition, when extender board 54 is in the first position, mid-size side portion 134 is generally aligned with post 254 as shown in FIG. 4. Post 254 is a hollow tube which extends through an aperture formed in end strut 100 so that portions of post 254 are positioned to lie on opposite sides of end strut 100. Thus, post 254 provides a passage through end strut 100.

A plunger 372 is received inside post 254 for sliding movement relative to post 254 as shown in FIG. 4. Plunger 372 includes a first end 374 on one side of end strut 100 and a flared second end 376 on the opposite side of end strut 100. A coil spring 378 is mounted on plunger 372 between post 254 and flared second end 376 of plunger 372. Spring 378 biases second end 376 of plunger 372 into engagement with straight portion 322 of release rod 310. When extender board 54 is in the first position and handle portion 342 of release lever 332 is moved in direction 364 toward corner portion 130 of frame 120 of extender board 54, plunger rod 334 moves in direction 368 and second end 352 of plunger rod 334 engages first end 374 of plunger 372 to move plunger 372 in a direction indicated by arrow 380, shown in FIG. 4.

As plunger 372 moves in direction 380, due to actuation of releasing assembly 330, plunger 372 moves release rod 310 into one of its releasing positions, thereby releasing gas spring 282 so that the position of back section 50 can be adjusted. Actuation of releasing assembly 330 coupled to the extender board 54 mounted to first side 40 of back section 50 causes first handle portion 324 to move away from the adjacent corner portion 110 of frame member 82 in a direction indicated by arrow 382 as shown in FIG. 4. Movement of first handle portion 324 in direction 382 causes release rod 310 to pivot about the second fulcrum point provided by the corner portion of second angled side wall 318. As release rod 310 pivots about the second fulcrum point, middle portion 314 of release rod 310 separates away from first angled side wall 316 of pivot block 294 to move plunger 300 toward the releasing position.

Actuation of releasing assembly 330 coupled to the extender board 54 mounted to second side 42 of back section 50 results in movement of release rod 310 that is a mirror image of the movement of release rod 310 described above with reference to actuation of release assembly 330 coupled to the extender board 54 mounted to first side 40 of back section 50. For example, actuation of releasing assembly 330 coupled to the extender board 54 mounted to second side 42 of back section 50 causes release rod 310 to pivot about the first fulcrum point provided by the corner portion of first angled side wall 316 and middle portion 314 of release rod 310 separates away from second angled side wall 318 of pivot block 294 to move plunger 300 toward the releasing position.

Thus, stretcher 30 includes pivot block 294 and release rod 310 which cooperate to provide stretcher 30 with a first releasing assembly that can be actuated to unlock back section 50 for pivoting movement about axis 92 and stretcher 30 includes a pair of second releasing assemblies 330, each of which can be actuated to actuate the first releasing assembly. In addition, the caregiver or surgeon can simultaneously grasp corner portion 130 of the respective frame member 120 and the handle portion 342 of the respective release lever 332 so that after actuation of either of second releasing assemblies 330, the caregiver or surgeon can manually pivot back section 50 relative to frame 32 of stretcher 30.

Figure 8:
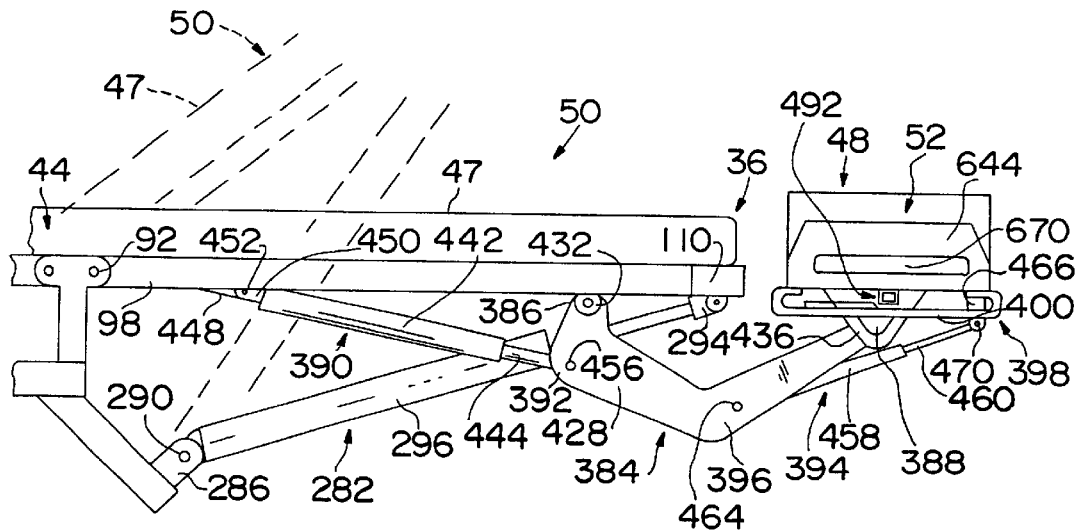
FIG. 8 is a side elevation view of the surgical stretcher of FIG. 1 showing the back section being locked in a flat table position by a first gas spring connecting the back section to the frame of the stretcher, a bracket coupling the head rest to the back section, the bracket being locked relative to the back section by a second gas spring connecting the bracket to the back section, and the head rest being locked in generally coplanar relation with the back section by a spring clutch connecting the head section to the bracket.
Figure 9:
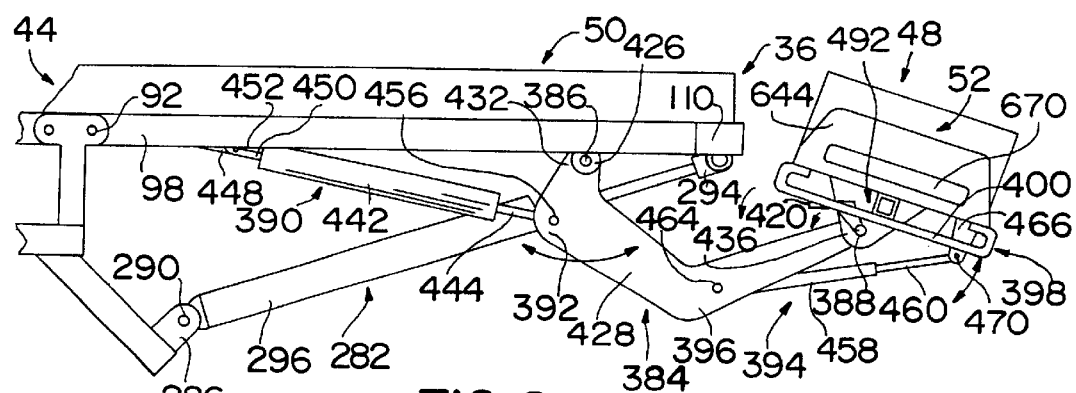
FIG. 9 is a view similar to FIG. 8 showing the bracket tilted downwardly relative to the back section, the head rest tilted rearwardly relative to the bracket, the bracket being pivotable relative to the back section about a transverse horizontal first pivot axis when the second gas spring is unlocked, and the head rest being pivotable relative to the bracket about a transverse horizontal second pivot axis when the spring clutch is unlocked.
Figure 10:
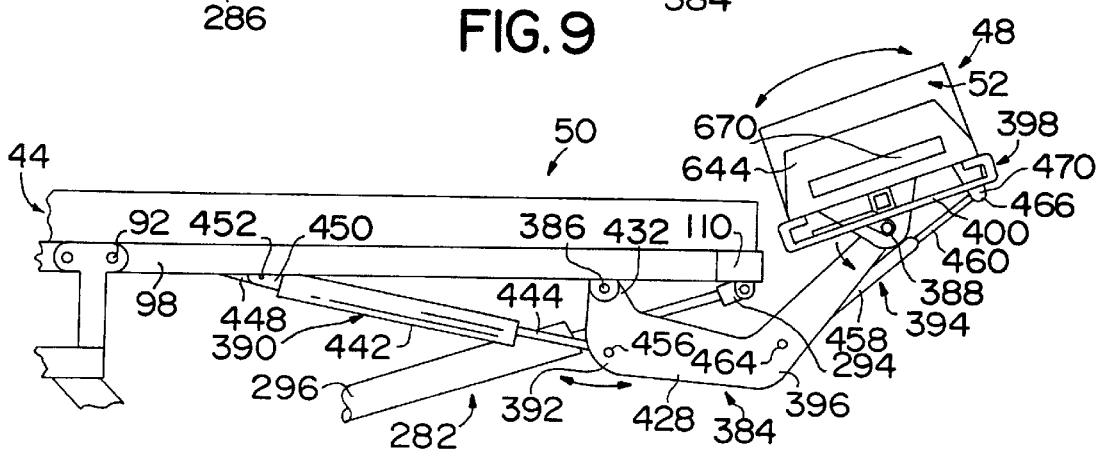
FIG. 10 is a view similar to FIG. 9 showing the bracket tilted upwardly relative to the back section and the head rest tilted forwardly relative to the bracket.

As previously described, stretcher 30 includes a head rest 48 coupled to back section 50. Stretcher 30 includes a mounting bracket 384 coupled to back section 50 for pivoting movement about a transverse first pivot axis 386 and head rest 48 is coupled to mounting bracket 384 for pivoting movement about a transverse second pivot axis 388 as shown in FIGS. 8–10. A first locking mechanism 390 connects a first elbow portion 392 of bracket 384 to back section 50 and a second locking mechanism 394 connects a second elbow portion 396 of bracket 384 to head rest 48.

First locking mechanism 390 is lockable to prevent bracket 384 from pivoting about axis 386 relative to back section 50 and second locking mechanism 394 is lockable to prevent head rest 48 from pivoting about axis 388 relative to bracket 384. Thus, when first and second locking mechanisms 390, 394 are both locked, the position of head rest 48 is fixed relative to back section 50. First locking mechanism 390 is releasable to allow manual adjustment of bracket 384 about axis 386 relative to back section 50 and second locking mechanism 394 is releasable to allow manual adjustment of head rest 48 about axis 388 relative to bracket 384.

A wire grip handle 398 is coupled to head rest 48 as shown, for example, in FIGS. 2 and 8–14. Grip handle 398 includes a pair of side handle portions 400 that extend longitudinally alongside each of sides 140, 142 of head rest 48 in spaced-apart relation therewith. Side handle portions 400 can be grasped to guide the movement of head rest 48 as the position of head rest 48 is manually adjusted. Grip handle 398 also includes an end handle portion 410 connecting side handle portions 400. End handle portion 410 can be grasped to help guide the movement of stretcher 30 along floor 64.

Figure 11:
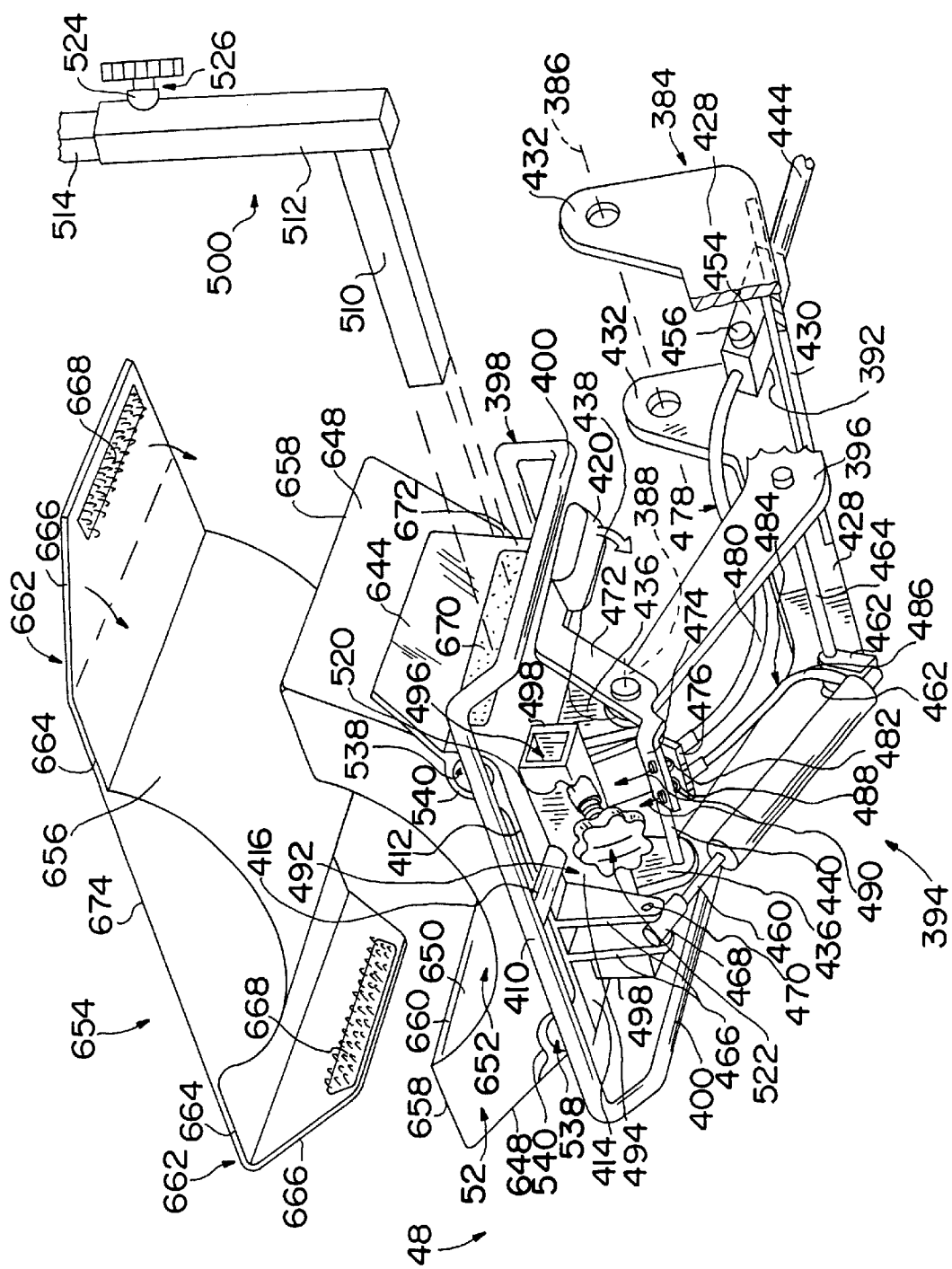
FIG. 11 is a perspective view of the head rest and bracket of FIG. 10 showing a head rest cushion filler above the head rest, a portion of a temporal wrist rest assembly beside the head rest and coupleable to the head rest, and release hardware coupled to the head rest and bracket, the release hardware being movable to simultaneously unlock the second gas spring and the spring clutch so that the head rest and bracket can be repositioned relative to the back section.

Head rest 48 includes a bottom plate 412 having a downwardly-facing bottom surface 414 and grip handle 398 includes a rear central branch 416 extending from end handle portion 412 and coupling to bottom surface 414 of bottom plate 412 as shown in FIG. 11. Grip handle 398 also includes a pair of front branches 418 that couple to bottom surface 414 of bottom plate 412. Although side handle portions 400, end handle portion 410, and branches 416, 418 of wire grip handle 398 are shown as being a single integral piece, it is within the scope of the invention as presently perceived for each side handle portion 400 and end handle portion 410 to be separate pieces that are configured to separately attach to head rest 48.

Stretcher 30 includes a pair of release buttons 420 coupled to head rest 48 and coupled to first and second locking mechanisms 390, 394. Release buttons 420 can be moved from a locking position to a releasing position to simultaneously unlock first locking mechanism 390 and second locking mechanism 394. Each release button 420 is positioned to lie between one of side handle portions 400 of grip handle 398 and a corresponding side 140, 142 of head rest 48. In addition, each release button 420 includes a thumb-engaging surface 422.

In use, the caregiver or surgeon can grasp side handle portions 400 of grip handle 398 with his or her fingers and can actuate release buttons 420 by pressing on thumb-engaging surfaces 422 with his or her thumbs to move release buttons 420 to the releasing position, thereby unlocking first and second locking mechanisms 390, 394. When first and second locking mechanisms 390, 394 are unlocked, the caregiver or surgeon can use side handle portions 400 of grip handle 398 to manually move head rest 48 to a desired position relative to back section 50.

After the caregiver or surgeon has moved head rest 48 to the desired position, the caregiver or surgeon can remove his or her thumbs from the thumb-engaging surfaces 422 and release buttons 420 will automatically return to the locking position so that first and second locking mechanisms 390, 394 simultaneously lock, thereby fixing head rest 48 in the desired position. Thus, the positioning of side handle portions 400 alongside head rest 48 in spaced-apart relation therewith and the positioning of release buttons 420 between side handle portions 400 and head rest 48 facilitates the easy unlocking and manual repositioning of head rest 48 relative to back section 50.

Head rest 48 can be moved to and locked in an infinite number of positions relative to back section 50. For example, bracket 384 and head rest 48 can be locked in a position in which head rest 48 is substantially aligned with back section 50 as shown in FIG. 8. Bracket 384 can pivot downwardly about axis 386 from the position shown in FIG. 8 to a lowered position, shown, for example, in FIG. 9.

Alternatively, bracket 384 can pivot upwardly about axis 386 from the position shown in FIG. 8 to a raised position, shown, for example, in FIG. 10. In addition, head rest 48 can tilt rearwardly about axis 388 from the position shown in FIG. 8 to a rearward inclined position, shown in FIG. 9, or, alternatively, head rest 48 can tilt forwardly about axis 388 from the position shown in FIG. 8 to a forward inclined position, shown in FIG. 10.

Frame member 82 of back section 50 includes a first intermediate strut 424 connecting side struts 98 between end strut 100 and base strut 84 as shown in FIG. 3. A pair of transversely spaced-apart flanges 426 extend away from intermediate strut 424. Bracket 384 includes a pair of side plates 428 and a spacer plate 430 connecting side plates 428 as shown, for example, in FIG. 11. Each plate 428 of bracket 384 includes a first terminal end portion 432 coupled to a respective flange 426 by a pivot pin 434 which extends transversely between flanges 426. Pivot pin 434 cooperates with flanges 426 to define pivot axis 386 about which bracket 384 pivots relative to back section 50.

Head rest 48 includes a pair of spaced-apart flanges 436 extending downwardly from bottom surface 414 of bottom plate 412 as shown in FIG. 11. Each plate 428 of bracket 384 includes a second terminal end portion 438 coupled to a respective flange 436 by a pivot pin 440 which extends transversely between flanges 436. Pivot pin 440 cooperates with flanges 436 to define pivot axis 388 about which head rest 48 pivots relative to bracket 384.

First terminal end portion 432 of bracket 384 is coupled to back section 50 between end strut 100 of frame 82 and axis 92 as shown in FIGS. 8–10. Side plates 428 of bracket 384 are curved so that sufficient clearance is established between bracket 384 and end strut 100 of frame 82 of back section 50 to allow bracket 384 to support head rest 48 at a position elevated above mattress 44. The clearance between bracket 384 and end strut also allows gas spring 282 to extend from flanges 286 to pivot block 294 between side plates 428 of bracket 384 as shown, for example, in FIG. 3. Thus, release rod 310, which is coupled to pivot block 294 adjacent to end strut 100 of frame member 82, is coupled to back section 50 at a position between terminal end portions 432, 438 of bracket 384.

In a preferred embodiment of stretcher 30, first locking mechanism 390 is a gas spring (hereinafter referred to as gas spring 390), although it is within the scope of the invention as presently perceived for locking mechanism 390 to include any of the locking mechanisms that were mentioned above with reference to actuator 282. Gas spring 390 includes a housing 442, a piston (not shown) inside housing 442, and a piston rod 444 coupled to the piston and extending out of housing 442. Gas spring 390 can be locked so that piston rod 444 can neither extend further out of housing 442 nor retract into housing 442, thereby preventing bracket 384 from pivoting about axis 386 relative to back section 50. Gas spring 390 can also be released so that the piston and piston rod 444 can extend and retract relative to housing 442, thereby allowing bracket 384 to pivot about axis 386 relative to back section 50.

Frame member 82 of back section 50 includes a second intermediate strut 446 connecting side struts 98 adjacent to base strut 84 as shown in FIG. 3. A pair of flanges 448 extend away from intermediate strut 446 toward end strut 100. Housing 442 of gas spring 390 includes an end 450 coupled to flanges 448 for pivoting movement by a pivot pin 452. Flanges 448 are coupled to intermediate strut 446 at a slightly off-center location so that gas spring 390 does not interfere with gas spring 282 as either of gas springs 390, 282 is operated. As shown, for example, in FIG. 11, piston rod 444 includes an end 454 coupled for pivoting movement to elbow portion 392 of one of side plates 428 by a pivot pin 456.

In a preferred embodiment of stretcher 30, second locking mechanism 394 is a spring clutch (hereinafter referred to as spring clutch 394), although it is within the scope of the invention as presently perceived for locking mechanism 394 to include any of the locking mechanisms that were mentioned above with reference to actuator 282. Spring clutch 394 includes a clutch housing 458 and a rod 460 slidably received by clutch housing 458. Spring clutch 394 also includes a coil gripping spring (not shown) received in clutch housing 458 and defining an interior region receiving a portion of rod 460. Spring clutch 394 can be locked so that the gripping spring constricts around rod 460 preventing rod 460 from sliding relative to the gripping spring and clutch housing 458. Spring clutch 394 can also be released so that the gripping spring loosens its grip on rod 460 allowing rod 460 to slide relative to the gripping spring and clutch housing 458.

A pair of flanges 462 are appended to housing 458 of spring clutch 394 as shown in FIG. 11. Flanges 462 are coupled to elbow portions 396 of side plates 428 by a pivot pin 464 which extends between elbow portions 396. Head rest 48 includes a pair of spaced-apart flanges 466 extending downwardly from bottom surface 414 of bottom plate 412 as shown in FIG. 11. An end 468 of rod 460 is coupled to flanges 466 by a pivot pin 470. Thus, when spring clutch 394 is locked, rod 460 cannot move relative to housing 458, thereby preventing head rest 48 from pivoting relative to bracket 384, and when spring clutch 394 is released, rod 460 can move relative to housing 458, thereby allowing head rest 48 to pivot relative to bracket 384.

As previously described, stretcher 30 includes release buttons 420 that can be engaged to simultaneously unlock first and second locking mechanisms 390, 394. Release buttons 420 are each coupled to opposite ends of pivot pin 440 by an arm 472. Arms 472 are each fixed to pivot pin 440 to rotate about axis 388 therewith. Thus, arms 472 and head rest 48 both pivot about axis 388 relative to bracket 384. By having arms 472 and head rest 48 both pivot about axis 388, release buttons 420 can be held in the same orientation relative to head rest 48 as head rest 48 is moved relative to bracket 384 about axis 388. In addition, if only one of release buttons 420 is pressed, both release buttons 420 move as result of the rigid coupling of arms 472 to pivot pin 440.

A transversely-extending tab 474 is appended to one of arms 472 and a plate 476 is appended to bottom plate 412 of head rest 48 as shown in FIG. 11. Plate 476 is bent so that a portion of plate 476 is positioned to lie in confronting relation with tab 474. A first Bowden wire 478 includes a sheath 480 extending from plate 476 to gas spring 390 and a cable 482 extending from tab 474 to gas spring 390 through sheath 480. A second Bowden wire 484 includes a sheath 486 extending from plate 476 to spring clutch 394 and a cable 488 extending from tab 474 to spring clutch 394 through sheath 486.

When release buttons 420 are pressed to the releasing position, thereby pivoting arms 472 and pivot pin 440 about axis 388, tab 474 is moved away from plate 476 so that cables 482, 488 are pulled relative to sheaths 480, 486, respectively, in the direction indicated by arrows 490, shown in FIG. 11. Movement of cables 482, 488 in respective directions 490 actuates mechanisms (not shown) inside of gas spring 390 and spring clutch 394, in a manner well known to those skilled in the art, to simultaneously unlock gas spring 390 and spring clutch 394 so that the position of head rest 48 can be adjusted. When release buttons 420 are no longer pressed, gas spring 390 and spring clutch 394 automatically lock to pull cables 482, 488 relative to sheaths 480, 486, respectively, in a direction opposite to direction 490 so that tab 474 is moved toward plate 476 and release buttons 420 are moved back to their locking positions adjacent to side handle portions 400 of grip handle 398.

A transversely-extending socket tube 492 having a square-shaped side wall 494 defining an interior region 496 is coupled to bottom surface 414 of bottom plate 412 of head rest 48 as shown in FIG. 11. Socket tube 492 has spaced-apart open ends 498 that provide access to interior region 496. Socket tube 492 is adapted to allow attachment of a temporal wrist rest assembly 500, a portion of which is shown in FIG. 11, to head rest 48.

Figure 12:
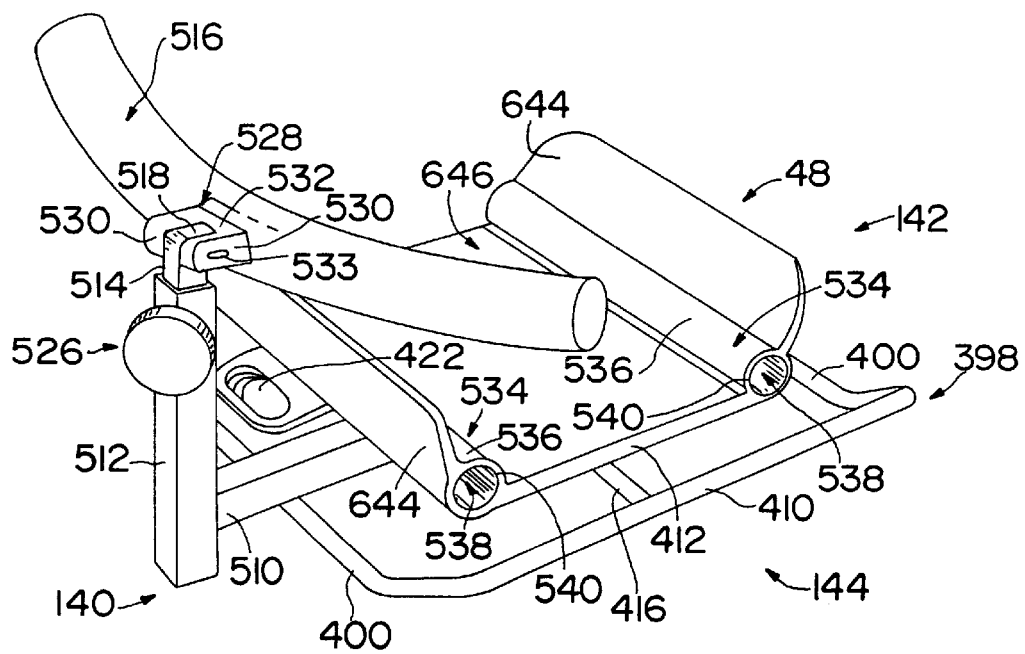
FIG. 12 is a perspective view of the head rest of FIG. 11 showing the head rest having a flat bottom plate, a longitudinally-extending socket tube appended to each side of the bottom plate, a side plate angling upwardly from each socket tube, and a transversely-extending bar of the temporal wrist rest assembly projecting underneath the head rest.

Temporal wrist rest assembly 500 includes a transversely-extending rod 510 and a first vertical rod 512 appended to an end of rod 510 as shown in FIGS. 11 and 12. Temporal wrist rest assembly 500 also includes a second vertical rod 514 coupled to first vertical rod 512 for telescoping movement and a temporal wrist rest 516 coupled to an upper end 518 of second vertical rod 514 for pivoting movement.

Transversely-extending rod 510 can be inserted into interior region 496 of socket tube 492 so that temporal wrist rest assembly 500 is mounted to head rest 48. Rod 510 can be inserted into interior region 496 through either of open ends 498 of socket tube 492 so that temporal wrist rest assembly 500 is adjacent to side 140 of head rest 48 or so that temporal wrist rest assembly 500 is adjacent to side 142 of head rest. Rod 510 extends above one of side handle portions 400 and beneath bottom plate 412 of head rest 48 when wrist rest assembly 500 is mounted to head rest 48. The cross-section of transversely-extending rod 510 is square-shaped so that side wall 494 of socket tube 492 engages rod 510 to prevent rod 510 from pivoting relative to socket tube 492.

A threaded cylinder 520 is appended to a bottom corner portion of socket tube 492 and a turn screw 522 is threadedly coupled to cylinder 520. Turn screw 522 can be turned to tighten rod 510 against socket tube 492 to prevent transverse movement of temporal wrist rest assembly 500 relative to head rest 48. Turn screw 522 can also be turned to loosen rod 510 from socket tube 492 to allow transverse movement of temporal wrist rest assembly 500 relative to head rest 48. Thus, the transverse position of wrist rest 516 relative to head rest 48 can be adjusted by moving rod 510 within socket tube 492 to a desired position and then turn screw 522 can be tightened to lock temporal wrist rest assembly 500 in the desired transverse position.

A threaded cylinder 524 is appended to a corner portion of first vertical tube 512 and a turn screw 526 is threadedly coupled to cylinder 524. Turn screw 526 can be turned to tighten second vertical rod 514 against first vertical rod 512 to prevent vertical telescoping movement of second vertical rod 514 relative to first vertical rod 512. Turn screw 526 can also be turned to loosen rod 514 from rod 512 to allow vertical telescoping movement of rod 514 relative to rod 512. Thus, the vertical position of wrist rest 516 relative to head rest 48 can be adjusted by moving rod 514 relative to rod 512 to a desired position and then turn screw 526 can be tightened to lock wrist rest 516 in the desired vertical position.

A bracket 528 is appended to wrist rest 516 and couples wrist rest 516 to second vertical rod 514. Bracket 528 includes a pair of pivot portions 530 and a stop portion 532 connecting pivot portions 530. Pivot portions 530 are coupled to upper end 518 of second vertical rod 514 by a pivot pin 533. Wrist rest 516 can pivot about pin 533 relative to second vertical rod 514 between a first position, shown in FIG. 12, in which stop portion 532 of bracket 528 engages one side of rod 514 to support wrist rest 516 in the first position and a second position (not shown) in which stop portion 532 of bracket 528 engages an opposite side of rod 514 to support wrist rest 516 in the second position. When wrist rest 516 is in the first position, the surgeon can rest his or her wrists on wrist rest 516 while performing surgery on the patient. When wrist rest 516 is in the second position, wrist rest 516 is moved away from head rest 48 so that the surgeon has greater access to the head of the patient.

Figure 13:
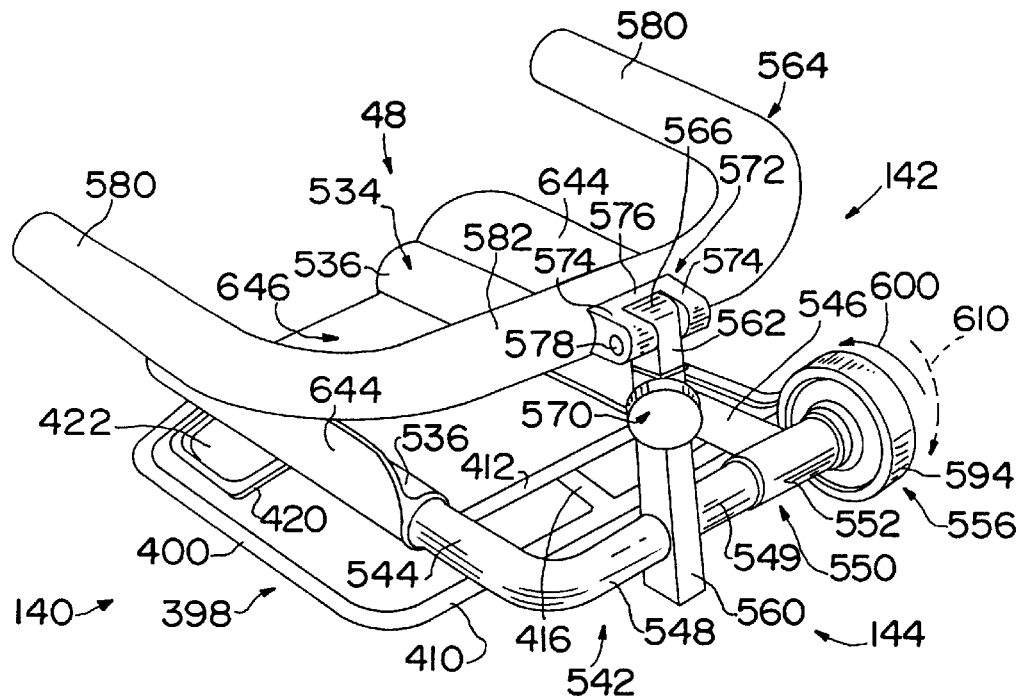
FIG. 13 is a view similar to FIG. 12 showing a wrist rest assembly coupled to the head rest by longitudinally-extending rods, each rod being received by a respective socket tube of the head rest, a wire grip handle coupled to the head rest beneath the bottom plate thereof, and a release button that can be pressed to unlock the second gas spring and the spring clutch, the release button being positioned to lie between a side handle portion of the wire grip handle and the head rest.

Head rest 48 includes a pair of longitudinally-extending socket tubes 534 appended to bottom plate 412 as shown in FIGS. 11–13. Socket tubes 534 each include a tube wall 536 defining an interior region 538 as shown best in FIG. 12. Socket tubes 534 each have an open end 540 that provides access to interior regions 538 of respective socket tubes 534. Socket tubes 534 are adapted to allow attachment of a wrist rest assembly 542 to head rest 48 as shown in FIG. 13.

Figure 14:
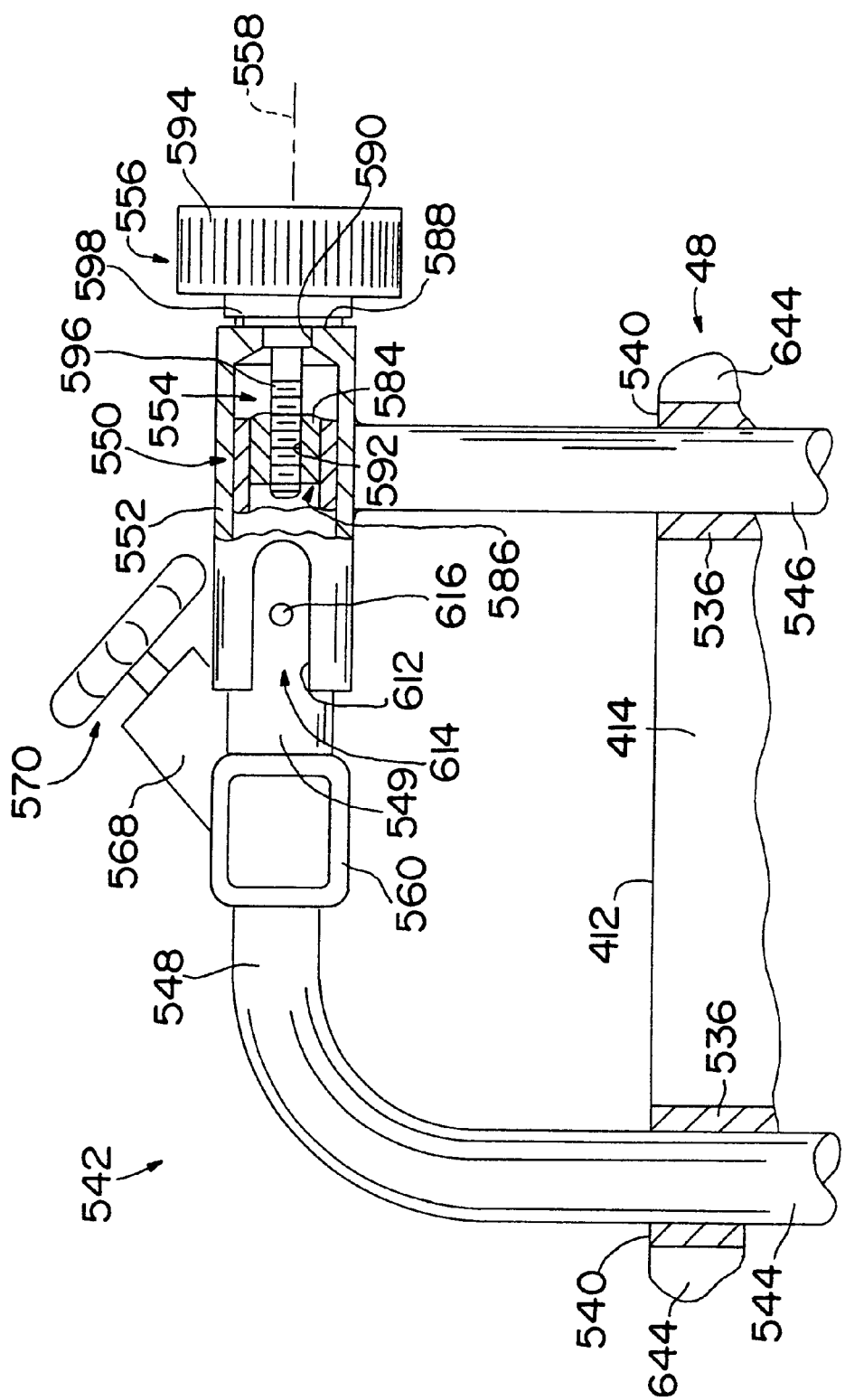
FIG. 14 is a bottom plan view of a portion of the wrist rest assembly, with portions broken away showing a transversely-extending end tube having a portion received in the interior region of an end socket tube and a turn screw coupled to both the end tube and the end socket tube.

Wrist rest assembly 542 includes a longitudinally-extending first rod 544 and a longitudinally-extending second rod 546. A transversely-extending end rod 548 is integrally appended to first rod 544 and a transversely-extending end socket tube 550 is appended to an end of second rod 546. Wrist rest assembly 542 further includes a first vertical rod 560 appended to an end portion of rod 548 and extending upwardly therefrom as shown in FIGS. 13 and 14. An end tube 549 of wrist rest assembly 542 is appended to first vertical rod 560 and extends transversely therefrom. Wrist rest assembly 542 also includes a second vertical rod 562 coupled to first vertical rod 560 for telescoping movement and a U-shaped wrist rest 564 coupled to an upper end 566 of second vertical rod 562 for pivoting movement.

End socket tube 550 includes a tube wall 552 defining an interior region 554 of end socket tube 550 and a portion of end tube 549 is received in interior region 554 as shown in FIG. 14. A turn screw 556 couples end tube 549 to end socket tube 550 so that rods 544, 546 are coupled together. Turn screw 556 can be rotated about an axis 558 to move end tube 549 relative to end socket tube 550, thereby moving first vertical rod 560 and end rod 548 which moves rod 544 relative to rod 546.

Longitudinally-extending rods 544, 546 can be inserted through open ends 540 of respective socket tubes 534 into interior regions 538 so that wrist rest assembly 542 is mounted to head rest 48. Wrist rest assembly 542 can be moved longitudinally relative to head rest 48 to a desired position and then turn screw 556 can be turned to tighten rods 544, 546 against tube walls 536 of socket tubes 534, thereby locking wrist rest assembly 542 from longitudinal movement relative to head rest 48. Turn screw 556 can also be turned to loosen rods 544, 546 from tube walls 536 of socket tubes 534 so that wrist rest assembly 542 can be longitudinally moved relative to head rest 48.

A threaded cylinder 568 is appended to a corner portion of first vertical tube 560 and a turn screw 570 is threadedly coupled to cylinder 568. Turn screw 570 can be turned to tighten second vertical rod 562 against first vertical rod 560 to prevent vertical telescoping movement of second vertical rod 562 relative to first vertical rod 560. Turn screw 570 can also be turned to loosen rod 562 from rod 560 to allow vertical telescoping movement of rod 562 relative to rod 560. Thus, the vertical position of wrist rest 564 relative to head rest 48 can be adjusted by moving rod 562 relative to rod 560 to a desired position and then turn screw 570 can be tightened to lock wrist rest 564 in the desired vertical position.

A bracket 572 is appended to wrist rest 564 and couples wrist rest 564 to second vertical rod 562. Bracket 572 includes a pair of pivot portions 574 and a stop portion 576 connecting pivot portions 574. Pivot portions 574 are coupled to upper end 566 of second vertical rod 562 by a pivot pin 578. Wrist rest 564 can pivot about pin 578 relative to second vertical rod 562 between a first position, shown in FIG. 13, in which stop portion 576 of bracket 572 engages one side of rod 562 to support wrist rest 564 in the first position and a second position (not shown) in which stop portion 576 of bracket 572 engages an opposite side of rod 562 to support wrist rest 564 in the second position.

Wrist rest 564 includes a pair of side portions 580 and an end portion 582 connecting side portions 580. When wrist rest 516 is in the first position, side portions 580 extend above sides 140, 142 of head rest 48 away from end portion 582 toward patient-support deck 34. The surgeon can rest his or her wrists on side portions 580 and end portion 582 of wrist rest 564 while performing surgery on the patient when wrist rest 564 is in the first position. When wrist rest 564 is in the second position, wrist rest 564 is moved away from head rest 48 so that the surgeon has greater access to the head of the patient.

As previously described, end tube 549 is received in interior region 554 of end socket tube 550 and turn screw 556 is coupled to both end tube 549 and end socket tube 550. An end plug 584 is inserted into an interior region 586 of end tube 549 and is fixed to end tube 549 as shown in FIG. 14. End socket tube 550 includes an end wall 588 adjacent to end plug 584. End wall 588 is formed to include an aperture 590 and end plug 584 is formed to include a threaded aperture 592.

Turn screw 556 includes a knob 594 and a threaded screw portion 596 extending away from knob 594 as shown in FIG. 14. Threaded screw portion 596 extends through aperture 590 formed in end wall 588 and is received by threaded aperture 592 formed in end plug 584 so that threaded screw portion 596 of turn screw 556 threadedly engages end plug 584. As knob 594 is rotated about axis 558, threaded screw portion 596 rotates relative to end plug 584 and end wall 588 about axis 558.

Knob 594 includes a tube-engaging surface 598 that can be moved into engagement with end wall 588 of end socket tube 550 as shown in FIG. 14. When rods 544, 546 are received in respective socket tubes 534, knob 594 can be turned in a tightening direction, indicated by arrow 600, shown in FIG. 13, until tube-engaging surface 598 of knob 594 engages end wall 588. Further rotation of knob 594 in direction 600, after initial engagement between tube-engaging surface 598 and end wall 588, causes threaded screw portion 596 to rotate within end plug 584 but engagement between tube-engaging surface 598 and end wall 588 prevents axial movement of threaded screw portion 596 along axis 558. Thus, after tube-engaging wall 598 engages end wall 588, rotation of knob 594 in direction 600 pulls end plug 584 and end tube 549 toward end wall 588 which causes rods 544, 546 to bind against tube walls 536 of socket tubes 534, thereby locking wrist rest assembly 542 from longitudinal movement relative to head rest 48.

Knob 594 can be turned in a loosening direction, indicated by dotted arrow 610, shown in FIG. 13, until rods 544, 546 are once again free to move relative to socket tubes 534 of head rest 48. After rods 544, 546 are loosened from socket tubes 534, wrist rest assembly 542 can be completely decoupled from head rest 48. End socket tube 550 includes an edge 612 defining a slot 614 as shown in FIG. 14. A post 616 is coupled to end tube 549 and is received in slot 614 so that, when wrist rest assembly 542 is decoupled from head rest 48, post 616 engages edge 612 to limit the amount by which end socket tube 550 and rod 546 can pivot relative to end tube 549 about axis 558.

Each of side portions 580 of wrist rest 564 can include open ends 618 that allow auxiliary medical equipment to be attached to wrist rest 564. For example, an air manifold assembly 620, shown in FIGS. 15 and 16, can be attached to wrist rest 564. Air manifold assembly 620 includes end caps 622 that mount to respective open ends 618 of side portions 580. Air manifold assembly 620 also includes a flexible tube 624 extending from each end cap 622. Flexible tubes 624 each couple to an end of a cylindrical air manifold 626 of air manifold assembly 620.

Air manifold 626 can include a center wall 628 that partitions air manifold 626 into an oxygen delivery side 630 and a carbon dioxide removal side 632. Center wall 628 divides an interior region of manifold 626 into two separate side-by-side interior regions. Sides 630, 632 of air manifold 626 are each formed to include a plurality of pores 634 that open into the respective side-by-side interior regions of air manifold 626. Thus, some of pores 634 are associated with oxygen delivery side 630 of air manifold 626 and some of pores 634 are associated with carbon dioxide removal side 632 of air manifold 626.

Each end cap 622 includes a tube connector 640 depending downwardly therefrom. An oxygen delivery hose 636 can be coupled to one of tube connectors 640 and a carbon dioxide removal hose 638 can be coupled to the other of tube connectors 640. End cap 622 associated with oxygen delivery hose 636, oxygen delivery side 630 of air manifold 626, and the flexible tube 624 therebetween all include internal passageways (not shown) in fluid communication with one another so that oxygen supplied through oxygen delivery hose 636 can flow through the internal passageways and out of the pores 634 associated with oxygen delivery side 630 of air manifold 626. Similarly, end cap 622 associated with carbon dioxide removal hose 638, carbon dioxide removal side 632 of air manifold 626, and the flexible tube 624 therebetween all include internal passageways (not shown) in fluid communication with one another so that, when suction is applied to carbon dioxide removal hose 638, the air in the vicinity of pores 634 associated with carbon dioxide removal side 632 of air manifold 626, can flow through the internal passageways and into carbon dioxide removal hose 638.

Figure 15:
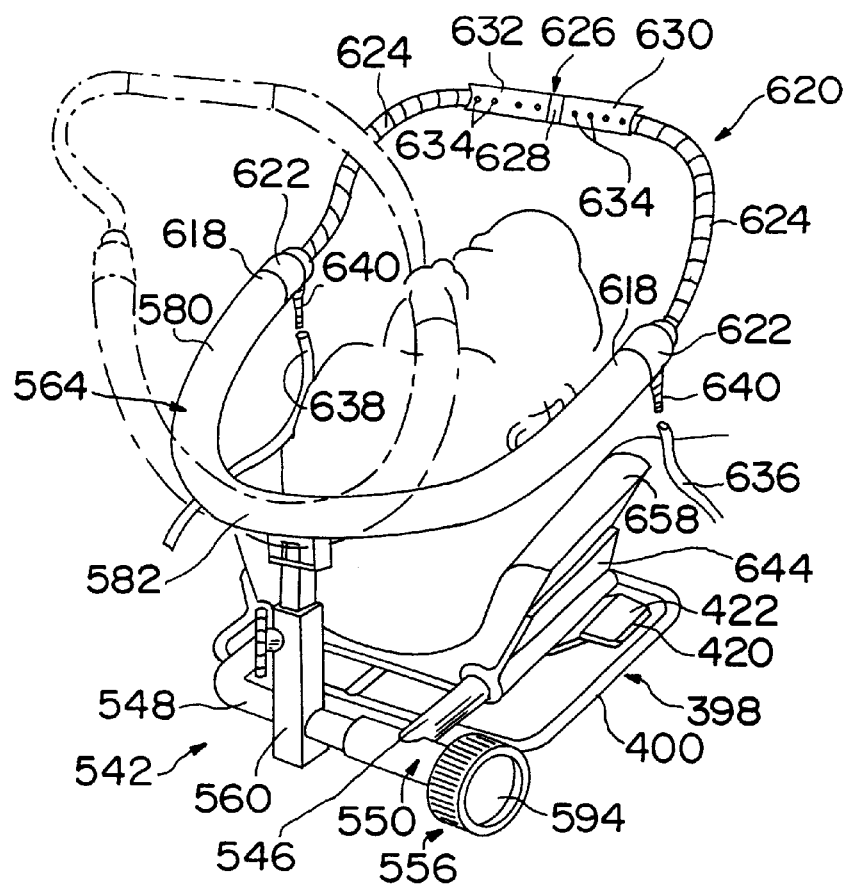
FIG. 15 is a perspective view of the head rest showing an air manifold assembly coupled to a U-shaped wrist rest of the wrist rest assembly, the wrist rest and air manifold assembly being pivotable away from a head of a patient to an out-of-the-way position (in phantom)
Figure 16:
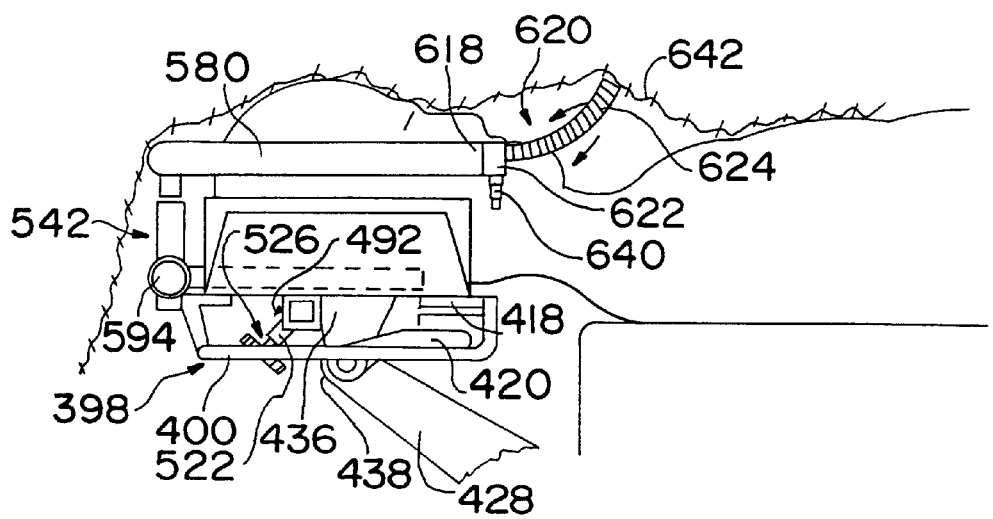
FIG. 16 is a side elevation view of the head rest of FIG. 15 showing the air manifold assembly and wrist rest assembly supporting a drape over the head of the patient to create a tented environment.

Flexible tubes 624 can be manipulated into an infinite number of orientations relative to wrist rest 564 so that air manifold 626 is at a desired position relative to the head of the patient supported by head rest 48. For example, it may be desirable to position air manifold 626 so that oxygen delivered to the patient through manifold 626 is directed toward the nose and mouth of the patient as shown in FIG. 16. Wrist rest 564 and air manifold assembly 620 can pivot away from the head of the patient, for example, to an intermediate out-of-the-way position as shown in FIG. 15 (in phantom) so that the access to the head of the patient is increased.

Flexible tubes 624 have sufficient stiffness to support a surgical drape 642 over the head of the patient to create a tented environment as shown in FIG. 16. Drape 642 can include a "sticky" side that adheres to the head of the patient and that adheres to the portions of air manifold assembly 620 and wrist rest 564 that support drape 642 above the head of the patient. The surgeon can cut a hole in drape 642 to expose the part of the head of the patient on which surgery is to be performed. Even when wrist rest 564 is covered by drape 642, the surgeon can rest his or her wrists on side and end portions 580, 582 of wrist rest 564.

As previously described, head rest 48 carries a head cushion 52 that supports the head of the patient. Head rest 48 includes a pair of spaced-apart side plates 644 angling upwardly from respective socket tubes 534 to define a head cushion-receiving space 646 therebetween as shown best in FIGS. 12 and 13. Although bottom plate 412, socket tubes 534, and side plates 644 of head rest 48 are shown as being a single integral piece, it is within the scope of the invention as presently perceived for some or all of these components to be separate pieces that are fastened together. For example, each socket tube 534 and the associated side plate 644 could be an extruded piece that fastens to a respective side of a single bottom plate 412. Other divisions of head rest 48 into separate pieces that fasten together are also possible.

Head cushion 52 includes angled side surfaces 648 and a bottom surface (not shown). When head cushion 52 is received in head cushion-receiving space 646, the bottom surface of head cushion 52 engages bottom plate 412 of head rest 48 and portions of side surfaces 648 engage companion side plates 644 so that head cushion 52 securely mates with head rest 48 within head cushion-receiving space 646. Fasteners (not shown), such as hook-and-loop fastener strips, can be attached to head cushion 52 and head rest 48 so that head cushion 52 is more securely coupled to head rest 48.

Head cushion 52 includes an upwardly-facing concave surface 650 that defines a head cradle 652 as shown, for example, in FIG. 11. Head cradle 652 is adapted to receive the head of the patient and concave surface 650 helps to stabilize the head of the patient during surgery. A cradle insert 654 can be coupled to head rest 48 to fill head cradle 652 when stretcher 30 is being used to transport the patient before and after surgery. Cradle insert 654 includes a downwardly-facing convex surface 656 that engages concave surface 650 of head cushion 52 when cradle insert 654 is inserted into head cradle 652.

Head cushion 52 includes a pair of upwardly-facing substantially planar surfaces 658, each of which extends between a respective upper edge 660 of concave surface 650 and the corresponding side surface 648. Cradle insert 654 includes a pair of fastening flaps 662, each of which includes a first portion 664 that extends over one of planar surfaces 658 when cradle insert 654 is received in head cradle 652, and each of which includes a second portion 666 that can be folded downwardly from its associated first portion 664 into engagement with side plates 644 of head rest 48.

A hook-and-loop fastener strip 668 is fixed to each second portion 666 of fastening flaps 662 and a companion hook-and-loop fastener strip 670 is fixed to an outer surface 672 of each side plate 644 of head rest 48. When cradle insert 654 is inserted into head cradle 652, fastening flaps 662 can be folded relative to head cushion 52 and head rest 48 so that strips 668 engage companion strips 670 to firmly secure cradle insert 654 in head cradle 652. Cradle insert 654 includes an upwardly-facing substantially planar surface 674 that is positioned to lie above convex surface 656. Surface 674 supports the head of the patient when cradle insert 654 is received in head cradle 652 of head cushion 52.

Figure 17:
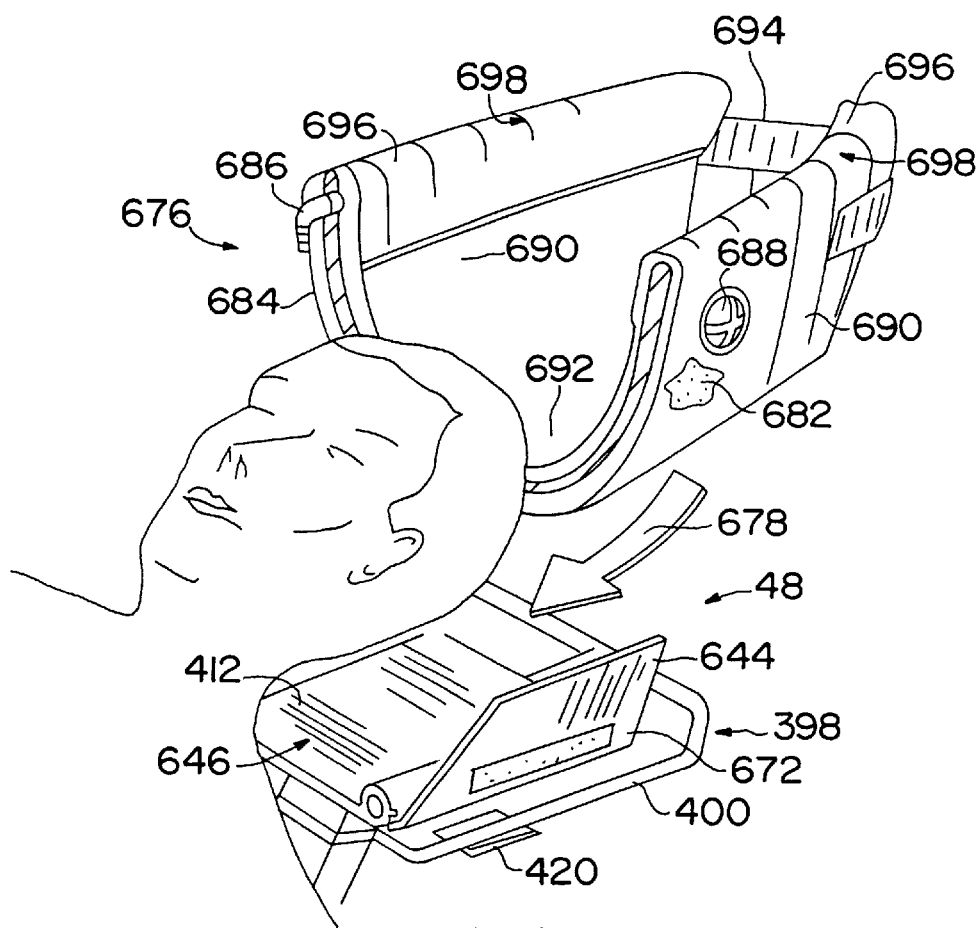
FIG. 17 is a perspective view of the head rest of FIG. 1 showing a vacuum pad being insertable between the head of the patient and the head rest, the vacuum pad having side walls with top edges that function as wrist rests.
Figure 18:
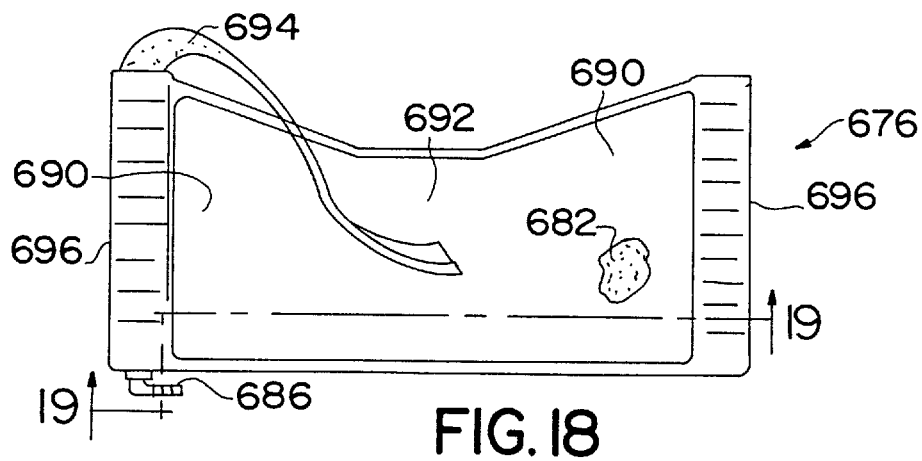
FIG. 18 is top plan view of the vacuum pad of FIG. 17 in a flat uncupped configuration showing the vacuum pad including a strap extending from one side thereof.
Figure 19:
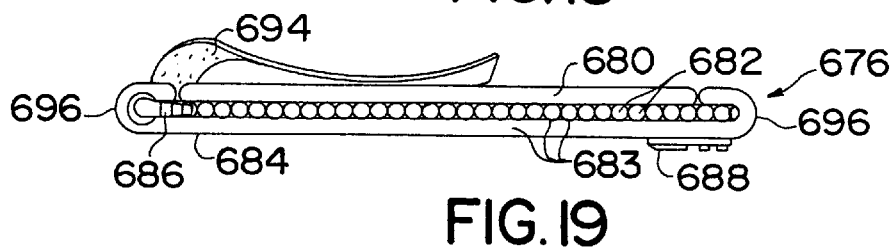
FIG. 19 is a sectional view of the vacuum pad taken along line 19—19 of FIG. 18 showing foam beads filling an interior region of the vacuum pad.

An alternative embodiment head cushion 676 is shown in FIGS. 17–19. Head cushion 52 can be removed from head cushion-receiving space 646 and head cushion 676 can be inserted into head cushion-receiving space 646 to replace head cushion 52 as indicated by double arrow 678 shown in FIG. 17. Compared to head cushion 52, head cushion 676 provides increased stabilization of the head of the patient, which is desirable during some head surgeries.

Head cushion 676 is a two-chamber vacuum pad (hereinafter referred to as vacuum pad 676) that includes a foam pad 680 in one of the chambers and a plurality of plastic beads 682 in the other of the chambers as shown in FIG. 19. Vacuum pad 676 includes a bag 684 having three sheets that are sealed together to define the chambers. In a preferred embodiment, bag 684 includes a first outer sheet made of Penn Nyla P079 material, a second outer sheet made of 15 mil urethane, and a middle sheet made of 6 mil urethane. Foam pad 680 is positioned to lie between the middle sheet and the first outer sheet. Plastic beads 682 are contained within a plurality of tubes 683 that are connected to form a bead pad. Some of tubes 683 are orthogonal to other of tubes 683 as shown in FIG. 19. The bead pad is positioned to lie between the middle sheet and the second outer sheet of bag 684.

Vacuum pad 676 includes a tube connector port 686 and a relief valve 688 as shown in FIG. 17. The bead pad which contains beads 682 is air permeable and the middle and second sheets of bag 684 are air impermeable. A hose (not shown) can be attached to tube connector port 686 and suction can be applied to the hose to draw air out of the second chamber and out of the bead pad through tube connector port 686. Drawing air out of the second chamber and bead pad causes beads 682 to be compressed together, thereby placing vacuum pad 676 in a rigid state.

When suction is not applied to the hose, air is permitted to enter the second chamber so that beads 682 are not compressed together and vacuum pad 676 is in a non-rigid state. In addition, relief valve 688 can be manually pressed so that air is permitted to enter the second chamber, thereby placing vacuum pad 676 in the non-rigid state. Pressing relief valve 688 places vacuum pad 676 in the non-rigid state even when suction is applied to the hose connected to tube connector port 686.

When vacuum pad 676 is in the non-rigid state, vacuum pad 676 is formable into an infinite number of configurations. For example, vacuum pad 676 can be formed from a flat uncupped configuration, shown in FIGS. 18 and 19, into a cupped configuration, shown in FIG. 17. Vacuum pad 676 has spaced-apart side wall portions 690 and a bottom portion 692 connecting side wall portions 690. Vacuum pad 676 includes a hook-and-loop fastener strap 694 extending away from one of side wall portions 690 and vacuum pad includes a companion hook-and-loop fastener strip (not shown) fixed to the other of side wall portions 690. A portion of strap 694 can be attached to the companion strip to help hold vacuum pad 676 in the cupped configuration as shown in FIG. 17.

When vacuum pad 676 is in the cupped configuration and carried by head rest 48, bottom portion 692 of vacuum pad 676 rests upon bottom plate 412 of head rest 48 and spaced-apart side wall portions 690 are adjacent to side plates 644 of head rest 48. Vacuum pad 676 includes edges 696 that face substantially upwardly when vacuum pad 676 is in the cupped configuration to provide a wrist rest surface 698 on which the wrists of the surgeon can rest during surgery. Edges 696 of side walls 690 are formable when vacuum pad 676 is in the non-rigid state. If the surgeon wishes to change the shape of wrist rest surfaces 698 during surgery when vacuum pad 676 is in the rigid state, the surgeon can press relief valve 688 to place vacuum pad 676 in the non-rigid state and then form edges 686 until wrist rest surfaces 698 are fashioned into the desired shape. The surgeon can then release relief valve 688 and vacuum pad 676 will return to the rigid state having wrist rest surfaces 698 fixed in the desired shape.

Figure 20:
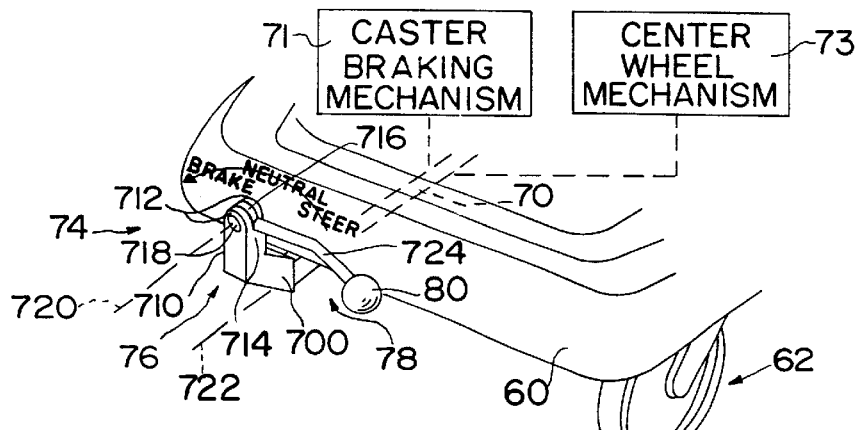
FIG. 20 is a perspective view of a head end lower portion of the surgical stretcher of FIG. 1 showing a flip-over pedal coupled to a longitudinally-extending brake-steer shaft by a yoke, the yoke being in an upright neutral position, and the flip-over pedal being pivotable in the direction of the double arrow relative to the yoke.
Figure 21:
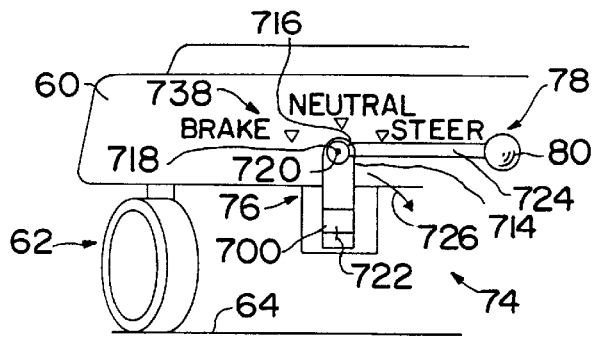
FIG. 21 is an end elevation view of the surgical stretcher of FIG. 20 showing the yoke in the upright neutral position, the flip-over pedal in a first orientation relative to the yoke, and the yoke being movable in the direction of the single arrow to pivot the brake-steer shaft about a longitudinally-extending axis in the direction of the single arrow.
Figure 22:
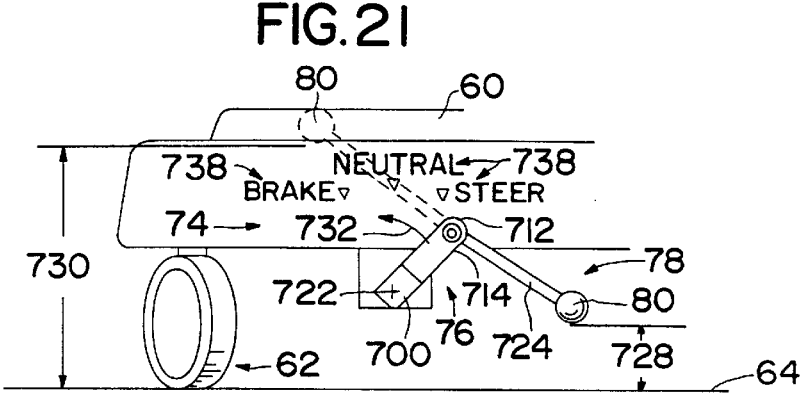
FIG. 22 is a view similar to FIG. 21 showing the flip-over pedal and yoke in a steering position and the flip-over pedal being movable relative to the yoke from the first orientation to a second orientation (in phantom)
Figure 23:
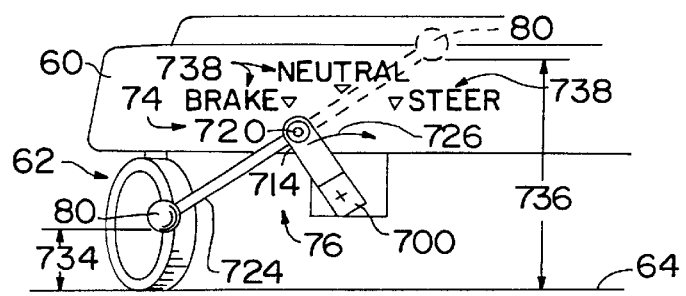
FIG. 23 is a view similar to FIG. 22 showing the flip-over pedal and yoke in a braking position and the flip-over pedal being movable relative to the yoke from the second orientation back to the first orientation (in phantom).

As previously described, stretcher 30 includes pedal assembly 74 which includes yoke 76 and flip-over pedal 78 coupled to yoke 76 for pivoting movement, as shown in FIGS. 20–23. Flip-over pedal 78 has a first orientation relative to yoke 76 in which distal end portion 80 of flip-over pedal is on one side of yoke 76, as shown in FIGS. 20–22, and flip-over pedal 78 has a second orientation relative to yoke 76 in which distal end portion 80 of flip-over pedal 76 is on the other side of yoke 76, as shown in FIG. 23, and as also previously described.

A bottom end 700 of yoke 76 is fixed to brake-steer shaft 70 and a top end 710 of yoke 76 is formed to include a pair of spaced-apart pivot portions 712 as shown in FIG. 20. Yoke 76 includes a stop portion 714 connecting pivot portions 712. Flip-over pedal 78 has a proximal end 716 coupled to pivot portions 712 of yoke 76 above stop portion 714 by a pivot pin 718. Pivot pin 718 cooperates with pivot portions 712 to define a pivot axis 720 about which flip-over pedal 78 can pivot relative to yoke 76.

Brake-steer shaft 70 is coupled to the lower frame of stretcher 30 for pivoting movement about a pivot axis 722. Axis 720 of flip-over pedal 78 is spaced apart from, and is substantially parallel with, axis 722 of brake-steer shaft 70. As brake-steer shaft 70 is moved between the steering and braking positions, axis 720 is always at a higher elevation above floor 64 than is axis 722 as shown in FIGS. 21–23. Thus, yoke 76 offsets flip-over pedal 78 upwardly to occupy a range of positions that is at a higher elevation relative to floor 64 than would be the case if flip-over pedal were connected to brake-steer shaft 70 to rotate about axis 722. Having flip-over pedal 78 at this heightened elevation increases the amount of room available on floor 64 in the vicinity of pedal assembly 74 for medical devices (not shown), such as foot pedal controllers used during surgery to operate associated medical equipment.

Brake-steer shaft 70 has a neutral position midway between the braking and steering positions, shown in FIGS. 20 and 21, in which yoke 76 is in an upright vertical orientation having axis 720 over axis 722. When brake-steer shaft 70 is in the neutral position, the center wheel is spaced apart from floor 64 and casters 62 are free to rotate and swivel.

Flip-over pedal 78 includes a rod 724 that connects distal end portion 80 to proximal end 716. Rod 724 is bent at the middle so that distal end portion 80 of flip-over pedal 78 is spaced apart from shroud 60 a sufficient distance to allow the caregiver or surgeon to step on distal end portion 80 without interference from shroud 60.

When flip-over pedal 78 is in the first orientation, one side of rod 724 engages stop portion 714 of yoke 76 and when flip-over pedal 78 is in the second orientation, an opposite side of rod 724 engages stop portion 714 of yoke 76. Engagement of rod 724 with stop portion 714 supports flip-over pedal 78 in the respective first and second orientations. Stop portion 714 of yoke 76 is formed so that flip-over pedal 78 rotates about axis 720 relative to yoke 76 through an angle of one hundred eighty degrees (180°) when pivoted between the first and second orientations.

When flip-over pedal 78 is in the first orientation, brake-steer shaft 70 can be rotated from the neutral position, shown in FIG. 21, in a clockwise direction 726 to the steering position, shown in FIG. 22, by application of a downward force to distal end portion 80 of flip-over pedal 78. The downward force on distal end portion 80 is transmitted through flip-over pedal 78 and yoke 76 to brake-steer shaft 70. Yoke 76 is in a first tilted orientation when brake-steer shaft 70 is in the steering position.

When brake-steer shaft 70 is in the steering position having yoke 76 in the first tilted orientation, flip-over pedal 78 can be pivoted from the first orientation, shown in FIG. 22 (in solid), to the second orientation, shown in FIG. 22 (in phantom). When brake-steer shaft 70 is in the steering position, distal end portion 80 is spaced apart from floor 64 by a first distance 728 if flip-over pedal 78 is in the first orientation and distal end portion 80 is spaced apart from floor 64 by a second distance 730 if flip-over pedal 78 is in the second orientation. Second distance 730 is larger than first distance 728 so that more room is available on floor 64 in the vicinity of pedal assembly 74 when distal end portion 80 is spaced apart from floor 64 by second distance 730.

When flip-over pedal 78 is in the second orientation while brake-steer shaft 70 is in the steering position, brake-steer shaft 70 can be rotated from the steering position, shown in FIG. 22, in a counterclockwise direction 732 through the neutral position to the braking position, shown in FIG. 23, by application of a downward force to distal end portion 80 of flip-over pedal 78. The downward force on distal end portion 80 is transmitted through flip-over pedal 78 and yoke 76 to brake-steer shaft 70. Yoke 76 is in a second tilted orientation when brake-steer shaft 70 is in the braking position.

When brake-steer shaft 70 is in the braking position having yoke 76 in the second tilted orientation, flip-over pedal 78 can be pivoted from the second orientation, shown in FIG. 23 (in solid), back to the first orientation, shown in FIG. 23 (in phantom). When brake-steer shaft 70 is in the braking position, distal end portion 80 is spaced apart from floor 64 by a third distance 734 if flip-over pedal 78 is in the second orientation and distal end portion 80 is spaced apart from floor 64 by a fourth distance 736 if flip-over pedal 78 is in the first orientation. Fourth distance 736 is larger than third distance 728 so that more room is available on floor 64 in the vicinity of pedal assembly 74 when distal end portion 80 is spaced apart from floor 64 by fourth distance 736.

Thus, flip-over pedal 78 can be selectively moved to the first and second orientations relative to yoke 76 and a downward force can be applied to distal end portion 80 of flip-over pedal 78 to move brake-steer shaft between the steering, neutral, and braking positions so that the braking of casters 62 and the position of the center wheel is controlled in a desired manner. Stretcher 30 includes indicia 738 affixed to shroud 60 for indicating the position of brake-steer shaft 70. After brake-steer shaft 70 has been moved to the desired position, flip-over pedal 78 can be moved to a position that maximizes the availability of room on floor 64 in the vicinity of pedal assembly 74.

Although the invention has been described in detail with reference to certain preferred embodiments, variations and modifications exist within the scope and spirit of the invention as described and as defined in the following claims.

What is claimed is:

1. An apparatus for supporting a patient, the apparatus comprising
    a frame,
    a patient-support deck coupled to the frame and configured to support the patient,
    a bracket coupled to the patient-support deck for pivoting movement about a transverse first pivot axis, the bracket extending away from the patient-support deck,
    a head rest coupled to the bracket for pivoting movement about a transverse second pivot axis, the head rest having first and second spaced-apart sides, and
    a grip handle coupled to the head rest, the grip handle having a side handle portion extending generally perpendicular to the first and second pivot axes alongside the first side of the head rest in spaced-apart relation therewith so that the side handle portion can be grasped to control pivoting movement of the head rest relative to the patient-support deck.

2. The apparatus of claim 1, further comprising a first locking mechanism coupling the bracket to the patient-support deck for locking the bracket relative to the patient-support deck, a second locking mechanism coupling the head rest to the bracket for locking the head rest relative to the bracket, and a release button coupled to the first and second locking mechanisms, the release button being movable to simultaneously unlock the first and second locking mechanisms so that the head rest can move relative to the bracket and so that the bracket can move relative to the patient-support deck.

3. An apparatus for supporting a patient, the apparatus comprising:
    a frame,
    a patient-support deck coupled to the frame and configured to support the patient,
    a bracket coupled to the patient-support deck for pivoting movement about a transverse first pivot axis, the bracket extending away from the patient-support deck,
    a head rest coupled to the bracket for pivoting movement about a transverse second pivot axis, the head rest having first and second spaced-apart sides,
    a grip handle coupled to the head rest, the grip handle having a side handle portion extending alongside the first side of the head rest in spaced-apart relation therewith so that the side handle portion can be grasped to control pivoting movement of the head rest relative to the patient-support deck,
    a locking mechanism for locking the head rest relative to the bracket, and
    a release button coupled to the locking mechanism and movable to unlock the locking mechanism so that the head rest can pivot relative to the bracket, the release button being positioned to lie between the side handle portion of the grip handle and the head rest so that the release button can be moved while the side handle portion is grasped.

4. The apparatus of claim 3, wherein the release button is coupled to the head rest for pivoting movement about the second pivot axis.

5. An apparatus for supporting a patient, the apparatus comprising:
    a frame,
    a patient-support deck coupled to the frame and configured to support the patient,
    a bracket coupled to the patient-support deck for pivoting movement about a transverse first pivot axis, the bracket extending away from the patient-support deck,
    a head rest coupled to the bracket for pivoting movement about a transverse second pivot axis, the head rest having first and second spaced-apart sides, a grip handle coupled to the head rest, the grip handle having a side handle portion extending alongside the first side of the head rest in spaced-apart relation therewith so that the side handle portion can be grasped to control pivoting movement of the head rest relative to the patient-support deck, a first locking mechanism coupling the bracket to the patient-support deck for locking the bracket relative to the patient-support deck, a second locking mechanism coupling the head rest to the bracket for locking the head rest relative to the bracket, and a release button coupled to the first and second locking mechanisms, the release button being movable to simultaneously unlock the first and second locking mechanisms so that the head rest can move relative to the bracket and so that the bracket can move relative to the patient-support deck, wherein the release button is positioned to lie between the side handle portion of the grip handle and the head rest so that the release button can be engaged and moved while the side handle portion of the grip handle is grasped.

6. An apparatus for supporting a patient, the apparatus comprising:

a frame, a patient-support deck coupled to the frame and configured to support the patient, a bracket coupled to the patient-support deck for pivoting movement about a transverse first pivot axis, the bracket extending away from the patient-support deck, a head rest coupled to the bracket for pivoting movement about a transverse second pivot axis, the head rest having first and second spaced-apart sides, and a grip handle coupled to the head rest, the grip handle having a side handle portion extending alongside the first side of the head rest in spaced-apart relation therewith so that the side handle portion can be grasped to control pivoting movement of the head rest relative to the patient-support deck, wherein the grip handle includes an end handle portion coupled to the head rest and extending transversely relative to the side handle portion so that the end handle portion can be grasped to maneuver the apparatus.

7. The apparatus of claim 6, wherein the head rest includes a downwardly-facing bottom surface and the grip handle is mounted to the bottom surface of the head rest.

8. The apparatus of claim 6, wherein the side handle portion and the end handle portion are positioned to lie below the head rest.

9. An apparatus for supporting a patient, the apparatus comprising:

a frame, a patient-support deck coupled to the frame and configured to support the patient, a bracket coupled to the patient-support deck for pivoting movement about a transverse first pivot axis, the bracket extending away from the patient-support deck, a head rest coupled to the bracket for pivoting movement about a transverse second pivot axis, the head rest having first and second spaced-apart sides, wherein the head rest includes a bottom plate and a transversely-extending socket tube coupled to the bottom plate, a grip handle coupled to the head rest, the grip handle having a side handle portion extending alongside the first side of the head rest in spaced-apart relation therewith so that the side handle portion can be grasped to control pivoting movement of the head rest relative to the patient-support deck, and a temporal wrist rest assembly, the temporal wrist rest assembly having a rod coupled to the socket tube, the rod of the temporal wrist rest assembly extending beneath the bottom plate of the head rest and above the side handle portion of the grip handle.

\* \* \* \* \*